(12) United States Patent
Claussen et al.

(10) Patent No.: US 12,274,606 B2
(45) Date of Patent: Apr. 15, 2025

(54) WEARABLE ARTICLE COMPRISING AN ELASTIC BELT LAMINATE

(71) Applicant: The Procter & Gamble Company, Cincinnati, OH (US)

(72) Inventors: Jan Claussen, Wiesbaden (DE); Zheng Bao, Beijing (CN); Koichi Morimoto, Beijing (CN); Lu Ye, Frankfurt (DE); Nancy Melenda Messer Myers, Lakeside Park, KY (US); Gueltekin Erdem, Beijing (CN); Rodrigo Rosati, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 818 days.

(21) Appl. No.: 17/529,778

(22) Filed: Nov. 18, 2021

(65) Prior Publication Data

US 2022/0071814 A1    Mar. 10, 2022

Related U.S. Application Data

(63) Continuation of application No. PCT/CN2021/108206, filed on Jul. 23, 2021, and a
(Continued)

(51) Int. Cl.
*A61F 13/49* (2006.01)
*A61F 13/15* (2006.01)
(Continued)

(52) U.S. Cl.
CPC .... *A61F 13/4902* (2013.01); *A61F 13/15203* (2013.01); *A61F 13/51* (2013.01);
(Continued)

(58) Field of Classification Search
CPC ............ A61F 13/4902; A61F 13/15203; A61F 13/51; A61F 2013/15406;
(Continued)

(56) References Cited

U.S. PATENT DOCUMENTS 8,282,617 B2    10/2012    Kaneda
8,777,918 B2    7/2014    Kuwano et al.
(Continued)

FOREIGN PATENT DOCUMENTS

CN      1299261 A    6/2001
CN    102316838 A    1/2012
(Continued)

OTHER PUBLICATIONS

PCT Search Report and Written Opinion for PCT/CN2021/108206 dated Nov. 12, 2021, 9 pages.
(Continued)

*Primary Examiner* — Camie S Thompson
(74) *Attorney, Agent, or Firm* — Charles R. Matson

(57) ABSTRACT

A wearable article comprising an elastic laminate with an inner web and an outer web being in a face to face relationship, and a skin-facing outer surface and a garment-facing outer surface. The elastic laminate has a total caliper when subjected to the NMR MOUSE method as defined herein, the total caliper having a first 200 µm sub-caliper corresponding to 200 µm of the total caliper starting from the skin-facing outer surface and extending towards the garment-facing outer surface, and a last 200 µm sub-caliper corresponding to 200 µm of the total caliper starting from the garment-facing outer surface and extending towards the skin-facing outer surface. The elastic laminate has a % Liquid Ratio in the first 200 micron sub-caliper to total caliper of less than 20% after 1 minute according to the NMR MOUSE method.

21 Claims, 13 Drawing Sheets

Related U.S. Application Data continuation-in-part of application No. PCT/CN2020/106125, filed on Jul. 31, 2020.

(51) Int. Cl.
  *A61F 13/51* (2006.01)
  *B32B 5/02* (2006.01)
  *B32B 5/06* (2006.01)
  *B32B 5/26* (2006.01)
  *B32B 7/08* (2019.01)

(52) U.S. Cl.
  CPC ............. *B32B 5/022* (2013.01); *B32B 5/06* (2013.01); *B32B 5/265* (2021.05); *B32B 7/08* (2013.01); *A61F 2013/15406* (2013.01); *A61F 2013/15512* (2013.01); *A61F 2013/1556* (2013.01); *A61F 2013/51004* (2013.01); *A61F 2013/51014* (2013.01); *A61F 2013/51019* (2013.01); *A61F 2013/51023* (2013.01); *B32B 2250/20* (2013.01); *B32B 2555/02* (2013.01)

(58) Field of Classification Search
  CPC .... A61F 2013/15512; A61F 2013/1556; A61F 2013/51004; A61F 2013/51019; A61F 2013/51023; B32B 5/265; B32B 5/06; B32B 5/022; B32B 7/08; B32B 2250/02
  USPC ........................................................ 442/328
  See application file for complete search history.

(56) References Cited

U.S. PATENT DOCUMENTS

| | | | |
|---|---|---|---|
| 8,840,600 | B2 | 9/2014 | Takeuchi |
| 8,932,274 | B2 | 1/2015 | Mukai |
| 9,622,922 | B2 | 4/2017 | Nelson |
| 9,633,933 | B2 | 4/2017 | Hayashi |
| 10,064,763 | B2 | 9/2018 | Takahashi et al. |
| 11,033,441 | B2 | 6/2021 | Xu et al. |
| 11,612,521 | B2 | 3/2023 | Ishikawa |
| 11,833,018 | B2 | 12/2023 | Dalal et al. |
| 2003/0065298 | A1 | 4/2003 | Krishnaswamy-mirle |
| 2003/0208175 | A1 | 11/2003 | Gross et al. |
| 2006/0047260 | A1 | 3/2006 | Ashton |
| 2010/0191207 | A1 | 7/2010 | Oba et al. |
| 2010/0310837 | A1 | 12/2010 | Bond et al. |
| 2010/0310845 | A1 | 12/2010 | Bond et al. |
| 2010/0312208 | A1 | 12/2010 | Bond et al. |
| 2010/0312212 | A1 | 12/2010 | Bond et al. |
| 2012/0238170 | A1 | 9/2012 | Weisman et al. |
| 2016/0332418 | A1 | 11/2016 | Jenkins et al. |
| 2019/0274895 | A1* | 9/2019 | Chen ................... A61F 13/4902 |
| 2023/0190541 | A1 | 6/2023 | Morimoto et al. |

FOREIGN PATENT DOCUMENTS

| | | |
|---|---|---|
| CN | 107920924 A | 4/2018 |
| CN | 110072499 A | 7/2019 |
| CN | 110087600 A | 8/2019 |
| JP | 2006326221 A | 12/2006 |
| JP | 2017113186 A | 6/2017 |
| JP | 6411323 B2 | 10/2018 |
| WO | 2010110154 A1 | 9/2010 |
| WO | 2019169989 A1 | 9/2019 |

OTHER PUBLICATIONS

All Office Actions; U.S. Appl. No. 17/527,543, filed Nov. 16, 2021.
All Office Actions; U.S. Appl. No. 17/528,316, filed Nov. 17, 2021.
All Office Actions; U.S. Appl. No. 17/528,491, filed Nov. 17, 2021.
PCT Search Report and Written Opinion for PCT/CN2020/106125 dated Apr. 12, 2021.
Unpublished U.S. Appl. No. 17/527,543, filed Nov. 16, 2021, to first inventor et. al.
Unpublished U.S. Appl. No. 17/528,316, filed Nov. 17, 2021, to first inventor et. al.
Unpublished U.S. Appl. No. 17/528,491, filed Nov. 17, 2021, to first inventor et. al.

* cited by examiner

WEARABLE ARTICLE COMPRISING AN ELASTIC BELT LAMINATE

CROSS REFERENCE TO RELATED APPLICATION

This application is a continuation of PCT Application No. PCT/CN2021/108206, filed on Jul. 23, 2021 and is a continuation-in-part of PCT Application No. PCT/CN2020/106125, filed on Jul. 31, 2020, both of which are incorporated herein by reference.

FIELD OF THE INVENTION

The present invention relates to a wearable article comprising an elastic laminate suitable for use in wearable articles which exhibits improved sweat management properties.

BACKGROUND OF THE INVENTION

Substrate materials such as nonwoven fabrics and laminates thereof, are commonly used for wearable articles such as absorbent articles. For example, absorbent articles typically use nonwoven substrate materials for both the skin facing side as well as the garment facing side of the articles, to control the movement of liquids and to provide a comfortable, conforming fit when the article is worn by a wearer. By comfortableness, what may be desired is a cloth-like substrate which is capable of effectively absorbing sweat and excess moisture from the skin and releasing them outside the article. Such is particularly desired, but not limited to, for absorbent articles by caregivers of young children, wherein skin health is closely associated with the absence of heat rashes and diaper rashes, but also with absorbent articles, such as pants, for incontinent adults, which are often older and also may have delicate skin. Heat rashes in the waist area may be associated with wetness or dampness in the waist area inside an absorbent article. It is a common practice for caregivers to check the degree of wetness or dampness by touching the waist area inside the absorbent article worn by a young child.

Elastic laminates having sweat management properties have been proposed, such as those described in Japanese Patent Application publications 2017/12319A and 2017/113186A. There is a need to provide elastic laminates with further improved sweat management properties, while being economic to make.

Elastic laminates used, e.g. for belts of absorbent pants are typically made of two nonwoven webs, which are joined to each other in a face to face relationship, with elastic strands sandwiched in between. In such laminates, a first nonwoven web (the inner nonwoven web) is facing the skin of the wearer and is in direct contact with the skin over a relatively large area of its surface. A second nonwoven web (the outer nonwoven web) is facing outwardly, away from the wearer, so it will commonly be in contact with the garment of the wearer. Often, the outer nonwoven web comprises an extended portion which is folded over the inner nonwoven web at the edge of the elastic laminate that forms the waist edge of the absorbent pant. Thereby, a more underwear-like, finished appearance of the pant is provided. Consequently, adjacent to the waist edge, the elastic laminate may comprise three nonwoven webs, namely the inner nonwoven web which is sandwiched between the outer nonwoven web and the extended, folded over portion of the outer nonwoven web.

The first and second nonwoven webs are typically both hydrophobic which has been found to lead to a relatively unsatisfactory performance in sweat management, i.e., in transporting sweat from the skin of the wearer through the laminate to the outside.

To address this drawback, it has been suggested to use a hydrophobic inner nonwoven web and an hydrophilic outer nonwoven web. However this technical approach may have certain limitations in that the sweat may not be sufficiently wicked in the plane of the belt itself and in that the liquid may accumulate in the outer layer providing a damp, wet feel to when touching the outer nonwoven web and potentially wetting the cloth worn over the absorbent pant. Moreover, in an elastic laminate of a pant belt having an extended, folded over portion of the outer nonwoven web at least a portion of the folded over portion will typically be in direct contact with a wearer's skin. In such configurations, transport of sweat from a wearer's skin tends to be reduced by the hydrophobic inner nonwoven web which is sandwiched between the hydrophilic folded over portion of the outer nonwoven web and the hydrophilic outer nonwoven web.

There is still a need for an elastic laminate with improved ability to wick liquid away from the wearer's skin in an efficient manner.

SUMMARY OF THE INVENTION

The invention relates to a wearable article comprising an elastic laminate. The elastic laminate comprising an inner web and an outer web being in a face to face relationship. Each of the inner and outer web are each a nonwoven web and each of the inner and outer web are comprised by the complete surface area of the elastic laminate.

The elastic laminate has a skin-facing outer surface and a garment-facing outer surface.

At least a portion of the inner web is in direct contact with the skin of the wearer, and at least a portion of the outer web forms a garment-facing outer surface of the wearable article.

The inner web has a first surface facing away from the outer web and a second surface facing towards the outer web, and the outer web has a first surface facing towards the inner web and a second surface facing away from the inner web.

The elastic laminate has a total caliper when subjected to the NMR MOUSE method as defined herein, the total caliper having a first 200 µm sub-caliper corresponding to 200 µm of the total caliper starting from the skin-facing outer surface of the elastic laminate and extending towards the garment-facing outer surface of the elastic laminate, and a last 200 µm sub-caliper corresponding to 200 µm of the total caliper starting from the garment-facing outer surface of the elastic laminate and extending towards the skin-facing outer surface of the elastic laminate.

The elastic laminate has a % Liquid Ratio in the first 200 micron sub-caliper to total caliper of less than 20%, or less than 18%, or less than 15% after 1 minute according to the NMR MOUSE method set out herein.

The elastic laminate may have a % Liquid Ratio in the last 200 micron sub-caliper to total caliper of not more than 20%, or not more than 15% after 1 minute according to the NMR MOUSE method set out herein. A % Liquid Ratio in the last 200 micron sub-caliper of less than 20% after 1 minute can reducing the wet feel of the garment-facing outer surface of the elastic laminate, e.g. when the wearer or the caregiver touches the garment-facing outer surface. This is due to the sweat being temporarily stored in the middle part of the laminate (in thickness direction, i.e. the portion of the elastic laminate that is in between the first and last 200 μm sub-caliper in thickness direction). Subsequently, the temporarily stored sweat can get transported via evaporation (i.e., transport in gaseous phase) through the garment-facing outer surface to the outside.

The elastic laminate defined above enables fast and reliable transport of liquid, such as sweat, away from the body of the wearer and through the elastic laminate to the outside.

Liquid transport away from the skin and through the laminate is measured by using NMR MOUSE (Nuclear Magnetic Resonance Mobile Universal Surface Explorer) methodology. NMR MOUSE is a portable device using an open NMR sensor to characterize fluid positioning inside a porous media structure (i.e. the elastic laminate). The method enables precise determination of liquid distribution at different points in time.

For the method, the skin-facing outer surface of an elastic laminate specimen is brought into contact with a solution of 0.9% sodium chloride (see detailed method description below) to simulate in use conditions when a person wears the wearable article. A % Liquid Ratio in the first 200 micron sub-caliper to total caliper of less than 20% after 1 minute means that, already 1 minute after the elastic laminate has been brought into contact with the liquid solution, more than at least 80% of the liquid within the elastic laminate has already been distributed away from the portion of the elastic laminate (here: 200 microns of the elastic laminate caliper) which is directly in contact with the skin of the wearer.

Having an elastic laminate comprising an a skin-facing outer surface and a garment-facing surface, it is essential that liquid moves quickly from the skin-facing outer surface to and through the thickness (=caliper) of the elastic laminate to enable efficient sweat management. Elastic laminates having a % Liquid Ratio in the first 200 micron sub-caliper to total caliper of less than 20%, or less than 18%, or less than 15% after 1 minute according to the NMR MOUSE method provide good sweat management, thus contributing to improved skin health.

The wearable article may have a longitudinal direction and a transverse direction. In the elastic laminate, elastic strands may be provided in between the inner and outer web. The elastic strands may extend along the transverse direction of the wearable article and may be spaced apart from each other in the longitudinal direction of the wearable article.

The elastic strands may be directly attached to the inner and/or to the outer web by means of an adhesive. The attachment may be continuously along the complete length of the elastic strands, intermittently along the complete length of the elastic strands or the elastic strands may only be attached to the inner and/or outer web at or adjacent to their ends.

The inner and outer web may both be non-elastic.

The elastic laminate may form a component of the wearable article which may be selected from the group consisting of an elastic belt, a waistband, a side panel, a continuous chassis, leg cuffs, and an outer cover.

In a preferred embodiment, the elastic laminate may be comprised by, or may form an elastic belt formed of a front belt and a back belt. Alternatively, the elastic laminate may form the complete garment-facing surface of the wearable article.

The front belt may form a front waist edge of the wearable article and the back belt may form a back waist edge of the wearable article.

The outer web of the elastic belt may comprise an extended portion which is extended beyond the front and back waist edge and which is folded over the inner web such that the fold forms the front and back waist edge and at least a portion of the elastic belt comprises the inner web sandwiched between the outer web and the folded over, extended portion of the outer web.

If the elastic laminate forms an elastic belt wherein the outer web comprises a folded over, extended portion as described in the previous paragraph, the % Liquid Ratio in the first 200 micron sub-caliper to total caliper being less than 20%, or less than 18%, or less than 15% after 1 minute according to the NMR MOUSE method set out herein, is determined in the area of the elastic belt which comprises the inner web sandwiched between the outer web and the folded over, extended portion of the outer web. Also, the % Liquid Ratio in the last 200 micron sub-caliper to total caliper being not more than 20%, or not more than 15% after 1 minute according to the NMR MOUSE method set out herein, may be determined in the area of the elastic belt which comprises the inner web sandwiched between the outer web and the folded over, extended portion of the outer web.

If the elastic laminate forms a front and a back belt of the wearable article, the front and back belt together form a ring-like elastic belt and the wearable article may further comprise a central chassis. The center of the front belt may be joined to a front waist panel of the central chassis, and the center of the back belt may be joined to a back waist panel of the central chassis. The remainder of the central chassis may form a crotch region. The front and back belt may each have a left side panel and a right side panel where the central chassis does not overlap, and the transverse edges of the front belt and the back belt may be joined by a seam to form a waist opening (consisting of the front and back waist edge) and two leg openings. The front belt and the back belt may be discontinuous of each other in the crotch region in the longitudinal direction.

The central chassis may comprise an outer cover layer on the garment-facing surface and a backsheet attached to the inner, wearer-facing surface of the outer cover layer. The longitudinal length of the outer cover layer may be longer than the longitudinal length of the crotch region and shorter than the longitudinal length of the backsheet.

The outer web may have a plurality of openings, such as apertures, at an Opening Rate of from about 5% to about 50%, preferably from about 5% to about 30%, according to the test method set out herein. The outer web may have an Effective Opening Area of from 0.1 mm$^2$ to 25 mm$^2$, preferably from 0.1 mm$^2$ to 10 mm$^2$, according to the test method herein.

The outer web may have a plurality of openings, such as apertures, at an Opening Rate of from 5% to 30%, preferably from 5% to 15%, and the outer web an Effective Opening Area of from 0.1 mm$^2$ to 25 mm$^2$, preferably from 0.1 mm$^2$ to 10 mm$^2$, according to the test method herein.

The outer web of the elastic belt may have a basis weight of from 5 g/m$^2$ to 45 g/m$^2$, and the outer web may have a basis weight of from 10 g/m$^2$ to 45 g/m$^2$.

The elastic laminate may have an elongation rate of at least 110% in at least one direction.

The outer web of the elastic belt may be hydrophilic.

The inner web may contain at least 20 weight-%, or at least 40 weight-%, or at least 50 weight-% of fibers selected from the group consisting of natural fibers, regenerated cellulose fibers and bio-based polymers, and combinations thereof, based on the total basis weight of the inner web.

The outer web may contain at least 20 weight-%, or at least 40 weight-%, or at least 50 weight-% of fibers selected from the group consisting of natural fibers, regenerated cellulose fibers and bio-based polymers, and combinations thereof, based on the total basis weight of the outer web.

BRIEF DESCRIPTION OF THE DRAWINGS

FIG. 5A shows the position of the sample holder determined with top marker without any specimen in between FIG. 5B shows the position of the sample holder determined with top marker with dry specimen in between.

DEFINITIONS

Figure 1A:
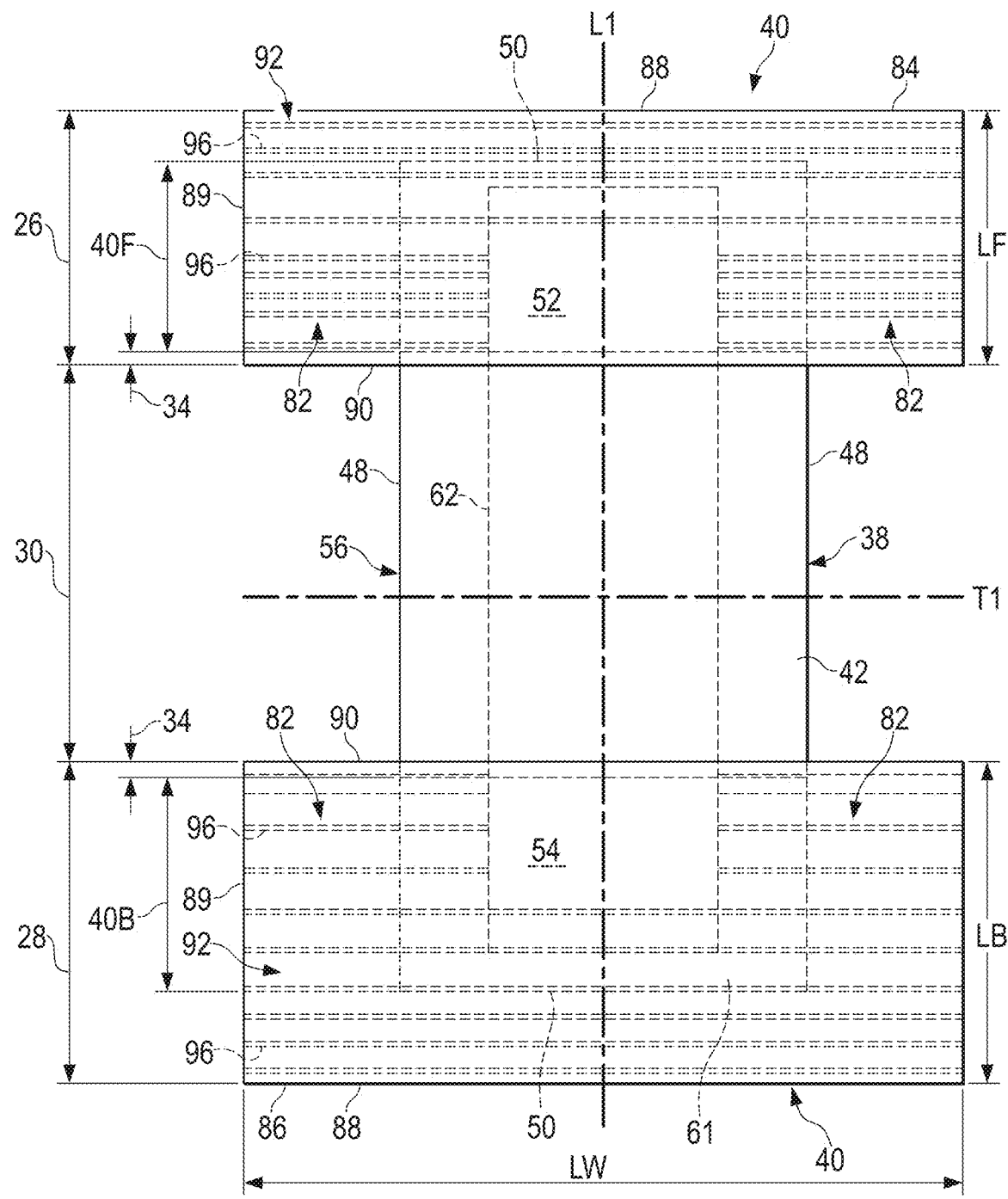
FIGS. 1A-1B are a schematic plan views of one embodiment of a wearable article of the present invention with the seams un-joined and in a flat uncontracted condition showing the garment facing surface

As used herein, the following terms shall have the meaning specified thereafter:

"Wearable article" refers to articles of wear which may be in the form of pants, taped diapers, incontinent briefs, feminine hygiene garments, wound dressings, hospital garments, and the like. Preferably, the wearable article of the present invention is a pant. The "wearable article" may be so configured to also absorb and contain various exudates such as urine, feces, and menses discharged from the body. The "wearable article" may serve as an outer cover adaptable to be joined with a separable disposable absorbent insert for providing absorbent and containment function, such as those disclosed in PCT publication WO 2011/087503A.

As used herein, "taped diaper" and "pant" refers to an absorbent article generally worn by babies, infants and incontinent persons about the lower torso to encircle the waist and legs of the wearer and that is specifically adapted to receive and contain urinary and fecal waste. In a pant, as used herein, the longitudinal edges of the first and second waist region are attached to each other to a pre-formed waist opening and leg openings. A pant is generally placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (i.e., with permanent side seams not intended to be torn upon prior to removal of the pant from the wearer for disposal). In a diaper, the waist opening and leg openings are only formed when the diaper is applied onto a wearer by (releasable) attaching the longitudinal edges of the first and second waist region to each other on both sides by a suitable fastening system.

"Taped diaper" refers to disposable absorbent articles which are applied on a wearer by tapes.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a taped diaper, a pant, sanitary napkin, sanitary pad or wet wipe for personal hygiene use, the disposable absorbent article is most often intended to be disposed after single use. The absorbent articles described herein are disposable.

"Longitudinal" refers to a direction running substantially perpendicular from a waist edge to an opposing waist edge of the article and generally parallel to the maximum linear dimension of the article. "Transverse" refers to a direction perpendicular to the longitudinal direction.

"Inner" and "outer" refer respectively to the relative location of an element or a surface of an element or group of elements. "Inner" implies the element or surface is nearer to the body of the wearer during wear than some other element or surface. "Outer" implies the element or surface is more remote from the skin of the wearer during wear than some other element or surface (i.e., element or surface is more proximate to the wearer's garments that may be worn over the present article).

"Body-facing" (also referred to as "skin-facing" herein) and "garment-facing" refer respectively to the relative location of an element or a surface of an element or group of elements. "Body-facing" implies the element or surface is nearer to the wearer during wear than another element of the same component. An example is the inner layer of the elastic laminate of the present invention wherein the inner layer (being an element of the elastic laminate) is nearer to the body of the wearer than the outer layer (being another element of the elastic laminate). "Garment-facing" implies the element or surface is more remote from the wearer during wear than another element of the same component. The garment-facing surface may face another (i.e. other than the wearable article) garment of the wearer, other items, such as the bedding, or the atmosphere. The "first 200 microns" referred to in the NMR test method below refer to the sub-caliper of the elastic laminate which starts from the skin-facing outer surface of the elastic laminate and extends through the thickness of the elastic laminate towards the garment-facing outer surface. The "last 200 microns" referred to in the NMR test method below refer to the sub-caliper of the elastic laminate which starts from the garment-facing surface of the elastic laminate and extends through the thickness of the elastic laminate towards the skin-facing outer surface.

"Proximal" refers to a portion being closer relative to the longitudinal center of the article, while "distal" refers to a portion being farther from the longitudinal center of the article.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Hydrophilic" describes surfaces of substrates which are wettable by aqueous fluids (e.g., aqueous body fluids) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is equal to or greater than 90° and the fluid does not spread spontaneously across the surface of the fiber. The contact angle test method used for the present invention is set out herein below.

"Extendibility" and "extensible" mean that the width or length of the component in a relaxed state can be extended or increased.

"Elasticated" and "elasticized" mean that a component comprises at least a portion made of elastic material.

"Elongation rate" means the state of elongation of a material from its relaxed, original length, namely an elongation rate of 10% means an elongation resulting in 110% of its relaxed, original length.

"Elongatable material", "extensible material", or "stretchable material" are used interchangeably and refer to a material that, upon application of a biasing force, can stretch to an elongation rate of at least 10% (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastic." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "non-elastic". For example, an elongatable material that has an initial length of 100 mm can extend at least to 150 mm, and upon removal of the force retracts to a length of at least 145 mm (i.e., exhibiting a 10% recovery).

As used herein, the term "nonwoven web" refers to a material which is a manufactured web/layer of directionally or randomly oriented fibers or filaments. The fibers may be of natural or man-made origin. Natural fibers may be selected from the group consisting of wheat straw fibers, rice straw fibers, flax fibers, bamboo fibers, cotton fibers, jute fibers, hemp fibers, sisal fibers, bagasse fibers, Hesper aloe fibers, miscanthus, marine or fresh water algae/seaweeds, silk fibers, wool fibers, and combinations thereof. Another group of fibers may also be regenerated cellulose fibers, such as viscose, Lyocell (Tencel®), rayon, modal, cellulose acetate fibers, acrylic fibers, cuprammonium rayon, regenerated protein fibers etc. Preferably, the natural fibers or modified natural fibers are selected from the group consisting of cotton fibers, bamboo fibers, viscose fibers or mixtures thereof. Preferably, the natural fibers are cotton fibers. Synthetic fibers may be selected from the group consisting of polyolefins (such as polyethylene, polypropylene or combinations and mixtures thereof), polyethylene terephthalate (PET), co PET, polylactic acid (PLA), polybutylene succinate (PBS), polyhydroxy alkanoid (PHA), nylon (or polyammide), or mixtures or combinations thereof. An alternative option is to use superabsorbent fibers, for example SAF™ which is a cross-linked terpolymer based on acrylic acid, which is partially neutralised to its sodium salt, commercially available from Technical Absorbents.

The fibers in a nonwoven web are consolidated by friction, and/or cohesion and/or adhesion, and/or by heat bonding, pressure bonding, heat and pressure bonding, and/or ultrasonic bond excluding paper and products which are woven, knitted, tufted, stitch-bonded. The fibers may be staple fibers (e.g., in carded nonwoven webs) or continuous fibers (e.g., in spunbonded or meltblown nonwoven webs).

Nonwoven webs can be formed by many processes such as meltblowing, spunlaying, solvent spinning, electrospinning, and carding, and the fibers can be consolidated, e.g., by hydroentanglement (in spunlaced nonwoven webs), air-through bonding (using hot air that is blown through the fiber layer in the thickness direction), needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g. by spraying, printing or foam application) and is subsequently cured to solidify.

The basis weight of nonwoven webs is usually expressed in grams per square meter ($g/m^2$).

In a spunlace nonwoven web the fibers have been carded as precursor web and then subjected to hydroentanglement to intermingle and intertwine the fibers with each other. Cohesion and the interlacing of the fibers with one another may be obtained by means of a plurality of jets of water under pressure passing through a moving fleece or cloth and, like needles, causing the fibers to intermingle with one another (hereinafter also referred to as "hydraulic interlacing"). Thus, consolidation of a spunlace nonwoven web is essentially a result of hydraulic interlacing. "Spunlace nonwoven web", as used herein, also relates to a nonwoven formed of two or more precursor webs, which are combined with each other by hydraulic interlacing.

The two or more webs, prior to being combined into one nonwoven by hydraulic interlacing, may have underdone bonding processes, such as heat and/or pressure bonding by using e.g. a patterned calendar roll and an anvil roll to impart a bonding pattern. However, the two or more webs are combined with each other solely by hydraulic interlacing. Alternatively, the spunlace nonwoven web is a single web, i.e., it is not formed of two or more precursor webs. Still in another alternative, the spunlace nonwoven web of the present invention may be formed of one precursor web onto which staple fibers are laid down. The staple fibers may not have been consolidated into a self-sustaining precursor web but the fibers are loosely laid onto the precursor web. The relatively loose staple fibers are then integrated and intertwined with each other and with the fibers of the underlying precursor web by (only) hydraulic interlacing. Spunlace nonwoven layers/webs can be made of staple fibers or continuous fibers (continuous fibers are also often referred to as filaments).

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The melting and re-solidification of the polymer provide the bonding between different fibers.

"Comprise," "comprising." and "comprises" are open ended terms, each specifies the presence of the feature that follows, e.g. a component, but does not preclude the presence of other features, e.g. elements, steps, components known in the art or disclosed herein. These terms based on the verb "comprise" encompasses the narrower terms "consisting essential of" which excludes any element, step or ingredient not mentioned which materially affect the way the feature performs its function, and the term "consisting of" which excludes any element, step, or ingredient not specified.

DETAILED DESCRIPTION OF THE INVENTION

Elastic Laminate of the Wearable Article

The elastic laminate of the wearable article comprises an inner web and an outer web being in a face to face relationship. The inner and outer web each are a nonwoven web. The inner and outer web are each comprised by the complete surface area of the elastic laminate.

The elastic laminate has a skin-facing outer surface and a garment-facing outer surface.

At least a portion of the inner web is in direct contact with the skin of the wearer, and at least a portion of the outer web forms an outer surface of the wearable article.

The inner web has a first surface facing away from the outer web and a second surface facing towards the outer web. The outer web has a first surface facing towards the inner web and a second surface facing away from the inner web.

The elastic laminate has a total caliper when subjected to the NMR MOUSE method as defined herein, the total caliper having a first 200 μm sub-caliper corresponding to 200 μm of the total caliper starting from the skin-facing outer surface of the elastic laminate and extending towards the garment-facing outer surface of the elastic laminate, and a last 200 μm sub-caliper corresponding to 200 μm of the total caliper starting from the garment-facing outer surface of the elastic laminate and extending towards the skin-facing outer surface of the elastic laminate. The % Liquid Ratio in the first 200 micron sub-caliper to total caliper is less than 20%, or less than 18%, ore less than 15% after 1 minute according to the NMR MOUSE method set out herein. The % Liquid Ratio in the last 200 micron sub-caliper to total caliper may be not more than 20%, or not more than 15% after 1 minute according to the NMR MOUSE method set out herein.

The inner web may be formed of at least 90 weight-% (based on the total weight of the inner web) of synthetic fibers. The inner web may be formed of 95 weight-% or of 100 weight-% of synthetic fibers. The synthetic fibers of the inner web may be selected from the group consisting of polyethylene, polypropylene, polyester, polylactic acid (PLA), and mixtures and combinations (such as co-polymers of polyethylene and polypropylene) thereof.

Alternatively or in addition, the outer web may be formed of at least 90 weight-% (based on the total weight of the inner web) of synthetic fibers. The outer web may be formed of 95 weight-% or of 100 weight-% of synthetic fibers. The synthetic fibers of the outer web may be selected from the group consisting of polyethylene, polypropylene, polyester, polylactic acid (PLA), and mixtures and combinations (such as co-polymers of polyethylene and polypropylene) thereof.

The outer web may comprise or may be formed of a first fibrous layer and a second fibrous layer. The fibers of the first fibrous layer may be less hydrophilic than the fibers of the second fibrous layer. The relationship of the fibers of the second fibrous layer having higher hydrophilicity than the fibers of the first fibrous layer comprises situations where the first fibrous layer is hydrophobic and the second fibrous layer is hydrophilic or the first and second fibrous layers are both hydrophilic wherein the second fibrous layer has higher hydrophilicity.

Alternatively or in addition, the inner web may comprise or may be formed of a first fibrous layer and a second fibrous layer. Unless explicitly mentioned otherwise herein below, the following description of the first and second fibrous layer is applicable irrespective whether the inner or outer web is formed of such first and second fibrous layer.

The fibers of the first fibrous layer may be less hydrophilic than the fibers of the second fibrous layer. The relationship of the fibers of the second fibrous layer having higher hydrophilicity than the fibers of the first fibrous layer comprises situations where the first fibrous layer is hydrophobic and the second fibrous layer is hydrophilic or the first and second fibrous layers are both hydrophilic wherein the second fibrous layer has higher hydrophilicity.

Alternatively or in addition to the difference in hydrophilicity, the fibers of the first fibrous layer may have smaller average fiber surface area/volume than the fibers of the second fibrous layer. A smaller average fiber surface area/volume (resulting in smaller average surface area per volume of the fibrous layer) can be obtained e.g., by using thicker fibers or, by using e.g., round fibers as fibers for the first fibrous layer and using shaped and/or thinner fibers for the second fibrous layer. Shaped fibers may have all shapes known in the art, such as multilobal. Examples of shaped fibers may be Coolmax fibers. Very thin fibers may be obtained via splittable fibers, for example splittable multicomponent fibers. Natural fibers may also be irregularly shaped, such as cotton fibers, offering increased average surface area per volume.

If any of the inner web, the outer web, or, if the inner or outer web comprises or is formed of a first and a second fibrous layer, the first fibrous layer and/or the second fibrous layer of the inner or outer web are formed of a mixture of different fibers, the average surface area per volume of that fibrous layer or of that web, respectively, is the average fiber surface area per volume of the different fibers used as determined by the average surface area per volume test set out below.

The average surface area per volume of the second fibrous layer may be at least 20 [1/mm], more preferably at least 30 [1/mm], more preferably at least 50 [1/mm], more preferably at least 60 [1/mm], even more preferably at least 100 [1/mm] higher than the average surface area per volume of the first fibrous layer.

The first and second fibrous layer may be integrally combined with each other, such that at least some of the fibers of the second fibrous layer interpenetrate the fibers of the first fibrous layer. Integrally combining the first and second fibrous layer can e.g. be achieved by spunlacing, i.e., the outer web can be a spunlace nonwoven web.

The first fibrous layer may be a preformed nonwoven, such as a spunbond nonwoven, which may be (point-) bonded with heat and/or pressure, e.g., by passing the layer between a pair of calendar rolls, one of which may have projections extending outwardly from the surface of the roll to impart a pattern of bonded areas on the spunbond layer; one or both of the calendar rolls may be heated). Alternatively, the preformed nonwoven forming the first fibrous layer may be a carded air-through bonded nonwoven. The second fibrous layer may be formed from staple fiber web which are laid onto the precursor nonwoven that forms the first fibrous layer.

Alternatively, though less preferred, the second fibrous layer may be a preformed nonwoven, such as the first fibrous layer described in the preceding paragraph.

The first and second fibrous layers may subsequently be combined by hydraulic interlacing.

If the first fibrous layer is a spunbond nonwoven precursor web, the web may be point bonded, by heat and/or pressure. In the bond points, the fibers of the spunbond nonwoven precursor web may be fused together. The point bonds may be relatively small and the overall bonded area may be relatively small. Such nonwoven webs are considered to be better suitable for being integrally combined with the second fibrous layer, as the fibers of the second fibrous layer can more easily entangle and interpenetrate with the fibers of the first fibrous layer. If the overall bonded area and the individual point bonds are excessively large, the first fibrous layer may also rupture if the first and second fibrous layer are integrally combined by hydraulic interlacing.

The first fibrous layer may form a first surface of the outer web and the second fibrous layer forms a second surface of the outer web. In the elastic laminate, the second surface faces towards the inner web and the first surface faces away from the inner web.

The first fibrous layer may form a first surface of the inner web and the second fibrous layer forms a second surface of the inner web. In the elastic laminate, the second surface faces towards the outer web and the first surface faces away from the outer web.

The outer web may form a part of an outermost surface of the wearable article, i.e., the surface which is facing towards the garment of the wearer in use. If the outer web comprises an extended portion which is folded over the inner web (as described in more detail below), this extended portion may contribute to the innermost surface of the wearable article.

Without being bound to theory, it is believed that sweat management of the elastic laminate can be improved by establishing a capillary gradient within the elastic laminate to drive fluid transport away from the wearer's skin, i.e., from inner, skin-facing outer surface of the laminate towards the center of the elastic laminate. It is of importance to transport moisture away from the surface of the elastic laminate which is in direct contact to the skin. Hence, if the second fibrous layer of the outer web has a higher capillary pressure than the inner web and higher than the first fibrous layer of outer web allows the sweat to be transported away from skin side of the elastic laminate towards the middle section (in relation to the thickness of the elastic laminate) of the elastic laminate. It has been found that sweat transport towards the garment-facing outer surface of the elastic laminate may be less desirable than fast fluid transport towards the center of the elastic laminate. From there, the liquid may be transported to the garment-facing outer surface of the elastic laminate at a lower rate, or may be transported to the garment-facing outer surface by evaporation. Thereby, the garment-facing outer surface (i.e., garment-facing surface) of the elastic laminate may provide a relatively dry feel (and in fact be dry) while at the same time enabling a dry skin-facing surface and dry skin.

Fast fluid transport away from the skin-facing outer surface of the elastic laminate is reflected by a % Liquid Ratio in the first 200 μm sub-caliper to total caliper of less than 20%, or less than 18%, or less than 15% after 1 minute according to the NMR MOUSE test method set out herein. Hence, less than 20% of the liquid is still present in the first 200 μm sub-caliper, while 80% or more have been transported away from the caliper which is directly adjacent to the wearer's skin (i.e., the first 200 microns).

In addition there is a growing desire to use natural fibers, such as cotton, silk, Lyocell, viscose and bamboo, in absorbent articles. Such use can contribute to improved sustainability of the article and is also considered healthier and more comfortable for the skin vs. synthetic fibers. However, while natural fibers readily absorb the fluid, such as a wearer's sweat, they do not easily transfer the liquid to other layers. Hence, nonwoven webs using natural fibers may potentially feel wet both on the skin of the wearer and on the surface facing the wearer's clothes. However, it has been found that by using natural fibers in a layer that forms the inside of an elastic laminate, the potential wet feel on the skin or from the outside can be eliminated.

In addition the presence of natural fibers, such as cotton or viscose, provides additional capacity for temporary storage of sweat until it is transported away via evaporation: in fact natural fibers, such as cotton and viscose, are known to be able to absorb moisture within the fiber itself at significantly higher levels than traditional synthetic fibers such as polypropylene or polyester. If desired this mechanism of increasing temporary sweat storage can be further enhanced via inclusion of superabsorbent fibers. The addition of natural fibers and/or superabsorbent fibers in the second fibrous layers allows to keep the moisture temporary in the middle of the elastic laminate, masking that moisture both on a skin-facing outer surface and the garment-facing outer surface. Herein below, a test method is set out to determine the moisture absorption capacity of a web.

As is known in the art of porous media science, capillary pressure of a fibrous material, such as the inner and outer web of the elastic laminate of the present invention, is proportional to both average surface area/volume of the fibers comprised in the fibrous material and to the hydrophilicity, determined via contact angle θ, of the fibers. Specifically, it is known that capillary pressure is proportional to the cosine of the contact angle cos θ. In other words higher average surface area per volume leads to higher capillary suction or capillary pressure in the material (i.e., in the inner and outer web). Likewise, higher hydrophilicity (and higher cos θ) also results in higher capillary suction or capillary pressure in that material (i.e., in the inner and outer web). Hydrophilicity and hydrophobicity are determined via contact angle θ. A web or fibrous layer having contact angle of 90° or less is hydrophilic and a web or fibrous layer having a contact angle of equal to or higher than 90° is hydrophobic. The lower the contact angle (below) 90°, the higher is the hydrophilicity of the web or fibrous layer, the higher the contact angle (above) 90°, the higher is the hydrophobicity of the web or fibrous layer.

The test methods to determine contact angle θ, and average surface area per volume are described below. These parameters can be determined for a web as well as for a fibrous layers of a web.

If the outer web is formed of a first and a second fibrous layer, the first and second fibrous layer may each have a contact angle θ and the inner web may have a contact angle θ. The cosine of the contact angle θ multiplied with the average surface area per volume of the second fibrous layer (cos θ×average surface area/volume) may be higher than the cosine of the contact angle θ multiplied with the average surface area per volume of the inner web.

The (cos θ×average surface area/volume) of the second fibrous layer may be at least 20 [1/mm], more preferably at least 30 [1/mm], even more preferably at least 50 [1/mm], and still more preferably at least 60 [1/mm], and even more preferably at least 100 [1/mm] higher than the (cos θ×average surface area/volume) of the inner web.

The (cos θ×average surface area/volume) of the second fibrous layer may not be more than 500 [1/mm], or not more than 400 [1/mm] higher than the (cos θ×average surface area/volume) of the inner web.

The cosine of the contact angle θ multiplied with the average surface area per volume of the second fibrous layer may be higher than the cosine of the contact angle θ multiplied with the average surface area per volume of the first fibrous layer.

The (cos θ×average surface area/volume) of the second fibrous layer may be at least 20 [1/mm], more preferably at least 30 [1/mm], even more preferably at least 50 [1/mm], and still more preferably at least 60 [1/mm], and even more preferably at least 100 [1/mm] higher than the (cos θ×average surface area/volume) of the first fibrous layer.

The (cos θ×average surface area/volume) of the second fibrous layer may not be more than 500 [1/mm], or not more than 400 [1/mm] higher than the (cos θ×average surface area/volume) of the first fibrous layer.

If the inner web is formed of a first and a second fibrous layer, the first and second fibrous layer may each have a contact angle θ and the outer web may have a contact angle θ. The cosine of the contact angle θ multiplied with the average surface area per volume of the second fibrous layer (cos θ×average surface area/volume) may be higher than the cosine of the contact angle θ multiplied with the average surface area per volume of the outer web.

The (cos θ×average surface area/volume) of the second fibrous layer may be at least 20 [1/mm], more preferably at least 30 [1/mm], even more preferably at least 50 [1/mm], and still more preferably at least 60 [1/mm], and even more preferably at least 100 [1/mm] higher than the (cos θ×average surface area/volume) of the outer web.

The (cos θ×average surface area/volume) of the second fibrous layer may not be more than 500 [1/mm], or not more than 400 [1/mm] higher than the (cos θ×average surface area/volume) of the outer web.

The cosine of the contact angle θ multiplied with the average surface area per volume of the second fibrous layer may be higher than the cosine of the contact angle θ multiplied with the average surface area per volume of the first fibrous layer.

The (cos θ×average surface area/volume) of the second fibrous layer may be at least 20 [1/mm], more preferably at least 30 [1/mm], even more preferably at least 50 [1/mm], and still more preferably at least 60 [1/mm], and even more preferably at least 100 [1/mm] higher than the (cos θ×average surface area/volume) of the first fibrous layer.

The (cos θ×average surface area/volume) of the second fibrous layer may not be more than 500 [1/mm], or not more than 400 [1/mm] higher than the (cos θ×average surface area/volume) of the first fibrous layer.

In addition natural fibers or fibers with high average surface area per volume, which may be present in the second fibrous layer of the inner or outer web, may also be present in the first fibrous layer of the inner or outer web as a result of the interpenetration, and protrude out from the first surface of the first fibrous layer of the inner or outer web. If the outer web comprises the first and second fibrous layer, such protruding fibers may contact skin and help liquid transfer from the skin to the outer web.

The contact angle is highly dependent on the hydrophilic/hydrophobic property of the material. Hence, the fibers of the first fibrous layer may be less hydrophilic than the fibers of the second fibrous layer. The fibers of the first fibrous layer may be hydrophobic and the fibers of the second fibrous layer may be hydrophilic. The relationship of the fibers of the second fibrous layer having higher hydrophilicity than the fibers of the first fibrous layer comprises situations where the first fibrous layer is hydrophobic and the second fibrous layer is hydrophilic. Alternatively, the first and second fibrous layers may both be hydrophilic wherein the second fibrous layer has higher hydrophilicity.

Alternatively or in addition, the fibers of the first fibrous layer may have smaller fiber average surface area per volume than the fibers of the second fibrous layer.

If the outer web is formed of a first and second fibrous layer, the inner web may have smaller fiber average surface area per volume than the fibers of the second fibrous layer. If the inner web is formed of a first and second fibrous layer, the outer web may have smaller fiber average surface area per volume than the fibers of the second fibrous layer.

It has been found that cos θ multiplied with the average surface area per volume (cos θ×average surface area/volume) is a good indication of the capillary pressure of a material, i.e., the higher the value for cos θ multiplied with the average surface area per volume is, the higher the capillary pressure.

Hence it is desirable that the second fibrous layer has a higher value of (cos θ×average surface area/volume) compared to the value of (cos θ×average surface area/volume) for the first fibrous layer.

If the outer web is formed of a first and second fibrous layer, it may also be desirable that the second fibrous layer has a higher value of (cos θ×average surface area/volume) compared to the value of (cos θ×average surface area/volume) for the inner web. If the inner web is formed of a first and second fibrous layer, it may also be desirable that the second fibrous layer has a higher value of (cos θ×average surface area/volume) compared to the value of (cos θ×average surface area/volume) for the outer web.

The second fibrous layer may be a carded layer and the fibers of the second fibrous layer may be staple fibers.

The first fibrous layer may be a spunbond layer formed of continuous fibers. Alternatively, the first fibrous layer may be a carded, air-through bonded layer formed of staple fibers.

The first and second fibrous layer may be integrally combined with each other by spunlacing. The fibers of the second fibrous layer may be provided on a surface of the first fibrous layer and, subsequently, the fibers of the second fibrous layer may be intertwined with each other and with the fibers of the first fibrous layer by subjecting water jets onto the fibers of the second web (hydraulic interlacing). When providing the fibers of the first fibrous layer on the second fibrous layer, the fibers of the first fibrous layer may not have been previously consolidated. For example synthetic fibers, such as polypropylene, may form a first fibrous layer (as a carded layer) of the inner or outer web and cotton fibers may form a second fibrous layer (also as a carded layer) of the inner or outer web. "Consolidated", as used herein, means that the fibers of a fibrous layer have not been bonded to each other, e.g., by providing a binder, by pressure, heat, or combinations thereof, and the fibers have also not been intertwined with each other by other means, such as by water jets (known as hydroentangling) or needle punching.

Vice versa, though less preferred, the first and second fibrous layer may be integrally combined with each other by spunlacing the fibers by providing the first fibrous layer on a surface of the second fibrous layer and, subsequently, the fibers of the first fibrous layer may be intertwined with the fibers of the second fibrous layer by subjecting water jets onto the fibers of the second web. When providing the fibers of the second fibrous layer on the first fibrous layer, the fibers of the second fibrous layer may not have been previously consolidated.

Alternatively to spunlacing, the fibers of the first and second fibrous layer may be integrally combined with each other by other known techniques, such as needle punching.

It is preferred that no adhesive (such as pressure sensitive adhesive or hot melt adhesive) and no binder is used to combine the first and the second fibrous layer.

At least 40% or at least 50%, or at least 70%, or all of the surface area of the elastic laminate does not comprise any additional material layers except the inner and outer web. The average surface area is determined when the elastic laminate is stretched such that the inner and outer web are flattened out, or such that the inner or outer web are flattened out, in case further elongation is not possible without breaking and rupturing one of the inner or outer web. If the outer web comprises an extended portion which is folded over onto the inner web, thereby providing a region in the elastic laminate which has three webs overlaying each other, namely the inner web, the outer web, and the folded over, extended portion of the outer web, then the folded over, extended portion is not considered an "additional material layer". Likewise, elastic strands are not considered to be additional material layers. Additional material layers are materials which are provided in addition to the inner and outer web (including any extended portions) and having a significant average surface area, such as films, additional nonwoven webs, or paper.

The second fibrous layer may comprise natural hydrophilic fibers, modified natural hydrophilic fibers or combinations thereof. The second fibrous layer may be completely formed of such natural hydrophilic fibers, modified natural hydrophilic fibers or combinations thereof. Alternatively, the second fibrous layer may comprise at least 25%, 50%, or at least 70%, or at least 90%, or at least 95%, by weight based on the total weight of the second fibrous layer, of natural hydrophilic fibers, modified natural hydrophilic fibers, hydrophilic synthetic fibers or combinations thereof. At least 25%, 50%, 70%, 90%, or at least 95% by weight based on the total weight of the second fibrous layer are hydrophilic fibers. Preferably, all fibers of the second fibrous layer are hydrophilic fibers.

All of the fibers of the first fibrous layer may be synthetic fibers, such as hydrophobic or hydrophilic synthetic fibers. Alternatively, synthetic fibers, such as hydrophobic synthetic fibers, may form at least 90%, or at least 95% by weight (based on the total weight of the first fibrous layer) of the first fibrous layer.

As the fibers of the first and second fibrous layer are integrally combined with each other (e.g., by spunlacing), the amount of natural hydrophilic fibers and/or modified natural hydrophilic fibers may gradually increases through the thickness of the inner or outer web (depending which of the inner and outer web may comprise a first and second fibrous layer) from the first surface towards the second surface of the inner or outer web.

The natural hydrophilic fibers or modified natural hydrophilic fibers of the second fibrous layer may be selected from the group consisting of cotton, bamboo, viscose, cellulose, silk, or mixtures or combinations thereof. Preferred modified natural hydrophilic fibers are regenerated cellulose fibers. E.g., viscose is a modified natural hydrophilic fiber in that it is made of regenerated cellulose fibers such as cellulose fibers from wood or bamboo or cotton.

The basis weight ratio of the first fibrous layer to second fibrous layer may be from 0.2 to 3, or from 0.2 to 2, or from 0.5 to 1.5, or from 0.5 to 1.

Alternatively to being formed of a first and second fibrous layer, the inner or outer web may be an air-through bonded carded nonwoven web. Alternatively, the inner web may be a spunbond web. If the inner or outer web is a spunbond web, the web may be (point-) bonded, by heat and/or pressure.

Elastic Laminate Used as a Belt for a Wearable Article

The elastic laminate may form the belt of a wearable article, such as a pant. The pant may be a disposable pant. A wearable article is described in more detail below.

If the elastic laminate forms the belt of a wearable article, e.g., a disposable pant, at least a portion of the inner web may be in direct contact with the skin of the wearer when the article is applied on a wearer, i.e., it may form at least a portion of the skin-facing outer surface of the wearable article. The outer web may form at least a portion of the garment-facing surface of the wearable article, which will typically be in contact with the clothes of the wearer and which may frequently be touched by a caregiver.

The inner and outer web may be directly joined with each other over an area of from about 5% to about 50%. By "directly joined" what is meant is that the inner web and the outer web are directly secured to each other by applying adhesive agents, ultrasound, pressure, heat, or the combination thereof. The percentage of area of the inner and outer webs that are directly joined with each other may vary depending on the joining method for forming the elastic laminate, as discussed in further detail below. The inner and outer webs may be directly joined with each other over an area of from about 5% to about 50% to provide appropriate sweat management property, while also helping to maintain integrity as an elastic laminate.

The outer web of the elastic laminate may have a plurality of openings at an Opening Rate of from about 5% to about 50% according to the measurements herein. By further provide a certain opening area for the outer web, there is provided multiple moisture transport channels are provided which can contribute to an effective liquid removal and transport to the outer web. The transport channels may be driven by capillary force gradient, and enhanced exposure to outside the laminate away from the skin.

Also, to provide a thickness gradient, the basis weight of the inner web may be not greater than the basis weight of the outer web. The inner web of the present invention is a nonwoven web which may have a basis weight of from about 5 g/m² to about 45 g/m², or from about 5 g/m² to about 35 g/m².

The first and second web may have a fiber diameter of from 1 μm up to 35 μm. The first and/or second web may also comprise nanofibers having a fiber diameter of below 1 μm. Fiber diameter, as known in the industry, may also be expressed in denier per filament (dpf), which is grams/9,000 meters of length of fiber. In the second web, the fiber diameter of the second fibrous layer may be lower than the fiber diameter of the first fibrous layer and of the first web. The inner web may be made by processes such as spunbond, spunlace, carded or air-laid; and may comprise fibers and/or filaments made of polypropylene (PP), polyethylene (PE), polyethylene phthalate (PET), polylactic acid/polylactide (PLA) or conjugate fibers (such as PE/PET, PE/PP, PE/PLA) as well as natural fibers such as cotton or regenerated cellulosic fibers such as viscose or lyocell. The inner web may be made by biodegradable material, or derived from renewable resources. Non-limiting examples of materials suitable for the inner web of the present invention include: 12-30 gsm air-through carded nonwoven substrate made of PE/PET bi-component staple fiber, such as those available from Beijing Dayuan Nonwoven Fabric Co. Ltd. or Xiamen Yanjan New Material Co. Ltd., and 8-30 gsm spunmelt nonwoven substrate comprising PP monofilament or PE/PP bi-component fibers, such as those available from Fibertex or Fitesa.

The inner web may preferably be relatively hydrophilic. If the outer web comprises an extended portion which is folded over the inner web, a certain level of hydrophilicity can help transport away from the skin of the wearer through the extended, folded portion of the outer web (which is no at least partly in direct contact with the wearer's skin). However, alternatively, though less preferred, the inner web may be inherently hydrophobic. The inner web may be provided hydrophobicity by treating with hydrophobic melt additives into polymer resin in the fiber making process, or applying hydrophobic additives after the nonwoven is formed.

Hydrophobic additives may be fatty acids originated from vegetable, animal, and/or synthetic sources. Fatty acids may range from $C_8$-$C_{30}$ fatty acid, or from $C_{12}$-$C_{22}$ fatty acid, or substantially saturated fatty acid. Hydrophobic additives may be fatty acid derivatives including fatty alcohols, fatty acid esters, and fatty acid amides. Suitable fatty alcohols include those derived from $C_{12}$-$C_{30}$ fatty acids. Suitable fatty acid esters include those fatty acid esters derived from a mixture of $C_{12}$-$C_{30}$ fatty acids and short chain monohydric alcohols, preferably from a mixture of $C_{12}$-$C_{22}$ saturated fatty acids and short chain monohydric alcohols. The hydrophobic melt additive may comprise a mixture of mono, di, and/or tri-fatty acid esters. An example includes fatty acid ester with glycerol having at least one alkyl chain, at least two, or three chains to a glycerol, to form a mono, di, or triglyceride. Suitable triglycerides include glycerol thibchenate, glycerol tristearate, glycerol tripalmitate, and glycerol trimyristate, and mixtures thereof. Exemplary hydrophobic melt additives include glyceryl tristearate, such as those commercially available as Techmer PPM15000. Hydrophobic agents may be fatty acid amides including those derivatives from a mixture of C12-C28 fatty acids (saturated or unsaturated) and primary or secondary amines such as erucamide, oleamide and behanamide.

Exemplary hydrophobic additives which may be applied after the nonwoven is formed include surfactants and silicone-based finishes, natural oil or wax such as cotton seed oil, beeswax and shea butter.

The inner web may optionally have a plurality of openings at an Opening Rate of from about 5% to about 30%, or from about 5% to about 15%, or from about 6% to about 8%, or from about 7% to about 15%, or from about 9% to about 25%, and an Effective Opening Area of from about 0.1 mm² to about 25 mm², or from about 0.1 mm² to about 10 mm², or from about 0.5 mm² to about 4 mm², or from about 4.0 mm² to about 8 mm², or from about 7 mm² to about 15 mm², according to the measurements herein.

The outer web of the elastic laminate may have a basis weight of from about 10 g/m² to about 45 g/m², or from about 10 g/m² to about 35 g/m², and may be adjusted such that the basis weight of the inner web is greater, equal or smaller than the basis weight of the outer web. The outer web may be made by processes such as spunbond, spunlace, carded or air-laid; and may comprise fibers and/or filaments made of polypropylene (PP), polyethylene (PE), polyethylene phthalate (PET), polylactic acid/polylactide (PLA) or conjugate fibers (such as PE/PET, PE/PP, PE/PLA) as well as natural fibers such as cotton or regenerated cellulosic fibers such as viscose or lyocell. Also, the outer web may be made by biodegradable material, or derived from renewable resources.

Hydrophilic additives may be polypropylene and polyethylene polymers such as those available from Techmer PM (Clinton, TN, US) sold under the trade name of Techmer PPM15560; TPM12713, PPM19913, PPM 19441, PPM19914, and PM19668. Hydrophilic additives may include, ionic surfactants, cationic surfactants, amphoteric surfactants or mixtures thereof. Exemplary hydrophilic additives include 100410 AF PE MB marketed by Ampacet, Irgasuf HL560 commercially available from Ciba Speciality Chemicals Inc., Hydrosorb 1001 commercially available from Goulston Technologies Inc., Cirrasol PP682 commercially available from Uniqema, Stantex S 6327 commercially available from Cognis, Silastol PST, Silastol PHP26 commercially available from Schill & Seilacher, Silwet L-7608 commercially available from Momentive Performance Materials, silicone surfactant with a polyethylene oxide chain and molecular weight above 700 g/mol by the name Polyvel S-1416 or VW 315 commercially available from Polyvel Inc.

Exemplary material for the outer web include: air-through carded nonwoven having a thickness of at least about 50 μm, or at least about 80 μm, or at least about 200 μm. The thickness may be less than 2000 μm, or less than 1500 μm, or less than 1250 μm. Such material may provide a soft lofty feeling to the garment-facing web. Suitable for the outer web of the present invention are air-through carded nonwoven material made of co-centric bicomponent fiber, crimping fiber made through core eccentric bicomponent filament or side by side bicomponent filament. Non-limiting examples of materials suitable for the outer web include: 12 g/m² to 45 g/m² air-through carded nonwoven substrate comprising PE/PET bi-component fibers, such as those available from Beijing Dayuan Nonwoven Fabric Co. Ltd. or Xiamen Yanjan New Material Co. Ltd., and 8-45 gsm spun melt nonwoven substrate comprising PP monofilament or PE/PP bi-component fibers, such as those available from Fibertex or Fitesa.

The basis weight and material thickness of the inner and outer webs herein is related to materials obtained from a finished product according to the "Preparation for Thickness and Basis Weight" below and measured by "Base caliper method-ASTM D 654 Standard Test Method for Thickness of Paper and Paper Board" with modification of the loading to 500 Pa, and by "Basis weight—ASTM D 756 Practice for Determination of Weight and Shape Changes of Plastics Under Accelerated Service Conditions", respectively. Total caliper of the elastic laminate is determined in the NMR MOUSE test method set out below.

The outer web may have a plurality of openings at an Opening Rate of from about 5% to about 50%, or from about 5% to about 30%, or from about 7% to about 15%, or from about 9% to about 25%, and an Effective Opening Area of from about 0.1 $mm^2$ to about 25 $mm^2$, or from about 0.4 $mm^2$ to about 2.0 $mm^2$, of from about 1.0 $mm^2$ to about 5 $mm^2$, or from about 4.0 $mm^2$ to about 8 $mm^2$, or from about 7 $mm^2$ to about 15 $mm^2$, according to the measurements herein.

Alternatively, or in addition, the inner web may haves a plurality of openings at an Opening Rate of from about 5% to about 50%, or from about 5% to about 30%, or from about 7% to about 15%, or from about 9% to about 25%, and an Effective Opening Area of from about 0.1 $mm^2$ to about 25 $mm^2$, or from about 0.1 $mm^2$ to about 10 $mm^2$, or from about 0.4 $mm^2$ to about 2.0 $mm^2$, or from about 0.5 $mm^2$ to about 4 $mm^2$, of from about 1.0 $mm^2$ to about 5 $mm^2$, or from about 4.0 $mm^2$ to about 8 $mm^2$, or from about 7 $mm^2$ to about 15 $mm^2$, according to the measurements herein For either the outer web and/or the inner web, the openings may be apertures, slits, or the like. Preferably, the openings are apertures. If the inner and outer web have openings, the openings of the inner web may be congruent with the openings of the outer web. Alternatively, if the inner and outer webs have openings, the openings of the inner web may not be congruent with the openings of the outer web. In a still further alternative, if the inner and outer webs have openings, some of the openings in the inner web may be congruent with the openings in the outer web, while the remaining openings in the inner web may not be congruent with the openings of the outer web.

The openings in the inner and/or outer web may be apertures having an aspect ratio of less than about 5. The aspect ratio of an opening is determined as such. The greatest dimension of the opening is measured, wherein the direction of the greatest dimension defines the first axis. The line perpendicular to the first axis is defines the second axis. The dimension of the opening along the second axis is measured, and defined the cross dimension. The aspect ratio is the greatest dimension divided by the cross dimension.

The openings may be made by female-male hot pin process, hole punching process, hydroentanglement process using water jets and a screen to create holes, and combinations thereof. The openings may be made by creating a plurality of weakened locations by heat or pressure followed by incrementally stretching, causing said nonwoven web to rupture at the weakened locations such as described in U.S. Pat. No. 5,628,097. Such rupturing method may be particularly useful for nonwovens using spunbonded fibers and meltblown fibers. The openings may be three-dimensional, nonhomogeneous, unaligned and forming a pattern as described in PCT Publication WO 2016/73712.

The inner web or the outer web may be devoid of openings (alternatively, both layers may be devoid of openings). Namely, the combination of the inner web and the outer web may provide a Relative Opening Rate of 100%, less than 100%, or less than about 50%, or less than about 15% according to the measurements herein. What is meant by Relative Opening Rate is the percentage of opening of the elastic laminate which matches the opening of the outer web. When there is only opening in the outer web, the Relative Opening Rate is 0%, while when the openings of the outer web and the inner web completely match, the Relative Opening Rate is 100%. In the present invention, the inner web may optionally have openings, and when so, the pattern and density of the openings may be changed so as to completely or partially match with those of the outer web.

The inner web and the outer web may be directly joined to each other over an area of from about 5% to about 50% by any means known in the art, such as by applying adhesive, ultrasound, pressure, or heat, for providing the elastic laminate of the present invention. The inner and outer web may be at least partially directly joined by adhesive agent. When adhesive agent is used for joining the inner and outer webs, the area in which adhesive agent is applied between the inner and outer webs is considered as area in which the webs are directly joined. When using adhesive agent as a joining means, the adhesive agent may be applied intermittently, such as in spiral pattern. Alternatively or additionally, the adhesive agent may be applied by a slot coat pattern for sake of better process control, wherein the area in which adhesive agent is applied is from about 5% to about 50%, or from about 5% to about 40%, or from about 5% to about 30% of the laminate planar area. Alternatively or additionally, the inner and outer webs may be at least partially directly joined by means which directly join the fibers of the inner and outer webs, such as by heat, pressure, or ultrasound.

The elastic laminate of the present invention may have an elongation rate of at least about 110% in at least one direction. Elasticity may be imparted by laminating an elastic body between the inner web and the outer web. The elastic body may preferably be a plurality of elastic strands, but may alternatively be elastic ribbons, or an elastic sheet. The webs and elastic bodies may be at least partially joined by means selected from the group consisting of; adhesive agent, heat, pressure, ultrasound, and combinations thereof. Referring to FIG. 1B, adhesive agent may be applied for joining the elastic bodies to the outer and/or inner web, and further applied via a slot coat in a pattern of panel adhesive agents 233 for joining the outer layer and the inner web. Alternatively or additionally, the elastic bodies may be joined by deforming the inner and/or outer web contacting the elastic body via ultrasound or heat, to anchor the elastic body against the inner and/or outer web. Though less preferred, the elastic body may be an elastic sheet; wherein ultrasound is applied at a certain energy level to the inner web, outer web, and elastic sheet, combined, such that the fibers of the inner web and the outer web come into direct contact with each other. These directly joined areas of fibers are also considered as area in which the inner and outer webs are directly joined.

Elastic laminates obtained by any of the aforementioned joining methods need not be embossed, or mechanically activated, beyond the force needed to at least partially directly join the layers. Thus, the elastic laminate may be economically made. The directly joined area may be measured by stretching the elastic laminate to an uncontracted condition, suitably with a force of 25N, and observing the planar area where the inner and outer layers are directly joined.

The Wearable Article

The present invention relates to a wearable article comprising an elastic laminate. The elastic laminate may form at least a part of a wearable article that is in direct contact with the skin.

The inner web is closer to the wearer than the outer web when the article is worn. The inner web may be in direct contact with the skin of the wearer when the article is worn. The outer web may form at least a part of the garment-facing outer surface of the wearable article.

Generally, the elastic laminate may be used as a component selected from the group consisting of elastic belts, waistbands, side panels, leg cuffs, and outer covers, of the wearable article.

The present elastic laminate is particularly useful as an elastic belt. The wearable article may be a pant. An exemplary pant is described in PCT Publication WO 2006/17718A. The pant may comprise a central chassis 38 to cover the crotch region of the wearer when the article is worn, a front belt 84 and a back belt 86 (hereinafter may be referred to as "front and back belts") comprising the elastic laminate of the present invention, the front and back belts 84, 86 forming a discrete ring-like elastic belt 40 (hereinafter may be referred to as "waist belt") extending transversely defining the waist opening. The wearable article 20 may be a uni-body type pant wherein the central chassis 38 is continuous with the front and back belt 84, 86, wherein the leg openings are continuously formed (not shown). The belt-type pant may be advantageous in that the central chassis 38 has better breathability, thus providing better sweat management for the entire wearable article.

Figure 1B:
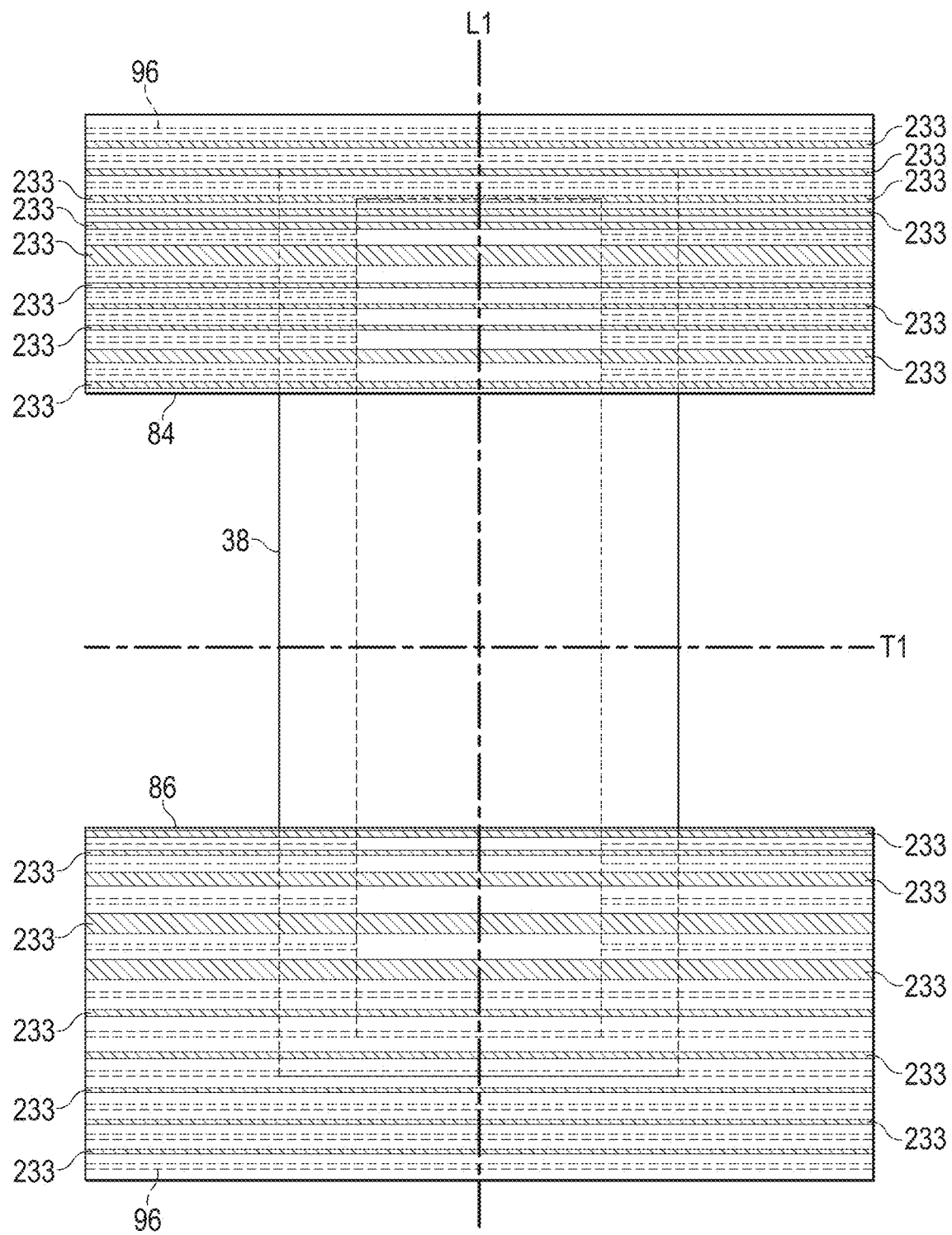

FIG. 1A is a perspective view of an example for a wearable article of the present invention of the pant with the seams un-joined and in its flat uncontracted condition showing the garment-facing surface. The wearable article has a longitudinal centerline LI which also serves as the longitudinal axis, and a transverse centerline T1 which also serves as the transverse axis. The wearable article has a body facing surface, a garment facing surface, a front region 26, a back region 28, a crotch region 30, and seams which join the front region 26 and the back region 28 to form two leg openings and a waist opening. As each of the inner and outer web are comprised by the complete surface area of the elastic laminate, the seams also comprise the inner and outer web of both, the front belt 84 and the back belt 86. At least a portion of or the entirety of the front belt 84, or at least a portion of or the entirety of the back belt 86, or the entire discrete ring-like elastic belt 40 may be made by the elastic laminate of the present invention. The front and back belts 84, 86 and the central chassis 38 jointly define the leg openings.

As exemplarily shown in FIGS. 1A and 2A-2C, the central chassis 38 may comprise a backsheet 60 and an outer cover layer 42 for covering the outer side of the backsheet 60. The backsheet 60 may be a water impermeable film. At least a portion of or the entirety of the outer cover layer 42 may be the elastic laminate of the present invention. The central chassis 38 may contain an absorbent core 62 for absorbing and containing body exudates disposed on the central chassis 38. As exemplified in in FIG. 1A, the central chassis 38 may have a generally rectangular shape, left and right longitudinally extending side edges 48 (hereinafter may be referred to as "side edge") and front and back transversely extending end edges 50 (hereinafter may be referred to as "end edge"). The central chassis 38 also has a front waist panel 52 positioned in the front region 26 of the wearable article, a back waist panel 54 positioned in the back region 28, and a crotch panel 56 between the front and back waist panels 52, 54 in the crotch region 30. The center of the front belt 84 is joined to a front waist panel 52 of the central chassis 38, the center of the back belt 86 is joined to a back waist panel 54 of the central chassis 38, the front and back belts 84, 86 each having a left side panel and a right side panel 82 where the central chassis 38 does not overlap. The central chassis 38 may comprise one or more leg cuffs per side for gasketing the leg opening. At least a portion of, or at least one of, or all of, the leg cuffs may be the elastic laminate of the present invention.

While not depicted, the wearable article of the present invention may be a taped diaper having a longitudinal axis, a transverse axis, a body facing surface, and a garment facing surface. The wearable article may have a central chassis comprising a front region, a back region, and a crotch region, each defined by a laterally extending line notionally divided along the longitudinal axis in 3 equal lengths. The front region and/or the back region may be provided with fastening members for fastening the article to configure the waist opening and leg openings. The waist opening may comprise a waistband. The fastening member may be made by a connecting part connecting to the central chassis, a stretchable side panel which is stretchable in the lateral direction, and an engaging part having engaging elements such as hooks. The front region and/or the back region may be provided with a landing zone for receiving the engaging elements of the fastening member. The landing zone may be loops engageable with the hooks. At least a portion of, or the entirety of, the waistband, side panels, or landing zones of the wearable article may be the elastic laminate of the present invention.

The ring-like elastic belt 40 of the pant of the present invention acts to dynamically create fitment forces and to distribute the forces dynamically generated during wear. The proximal edge 90 is located closer than the distal edge 88 relative to the crotch panel 56 of the central chassis 38. The front and back belts 84, 86 may be joined with each other only at the side edges 89 at the seams to form a wearable article having a waist opening and two leg openings. Each leg opening may be provided with elasticity around the perimeter of the leg opening. For the belt-type pant, the elasticity around the leg opening may be provided by the combination of elasticity from the front belt 84, the back belt 86, and any from the central chassis 38.

The front belt 84 and back belt 86 of the pant are configured to impart elasticity to the belt 40. The front belt 84 and the back belt 86 may each be formed by the present elastic laminate comprising a plurality of elastic bodies 96 running in the transverse direction, an inner web 94, and an outer web 92. Optionally an outer sheet fold over 93 which is an extended portion of the outer web (=second web) may be formed by folding the extended portion of the outer web. Alternatively, though less preferred, an inner sheet fold over 95 may be formed, which is an extension of the inner sheet material may be formed by folding the inner sheet material. The outer web 92 may be made of the same nonwoven substrate of the present invention as the outer cover layer 42 to provide integral aesthetic and tactile senses for the article. The outer web fold over is preferably provided around the waist opening 88 of the wearable article.

When the central chassis 38 contains an absorbent core, some or all of the areas of the front or back belt 84, 86 overlapping the absorbent core may be made devoid of elasticity. Referring to FIG. 1A, areas of the front waist panel 52 and back waist panel 54 in which the elastic bodies 96 are deactivated are shown in blank. For example, as seen in the back belt 86, the elastic bodies 96 overlapping the absorbent material non-existing region 61 and toward the distal edges of the absorbent core 62 may be disposed in active elasticity for good fit of the central chassis 38. This may be advantageous in preventing leakage.

Providing an outer fold over 95, 93 is advantageous for avoiding the waist opening 88 ending in sharp edges of the front or back belt 84, 86. Further, any elastic bodies 96 in the front or back belt 84, 85 may be disposed at least about 2 mm away, or from about 5 mm to about 9 mm away from the waist opening, to avoid the waist opening to be sharp, and also to ensure that any elastic body is not accidentally exposed during manufacture or use. The outer web fold over 95, 93 may extend toward the proximal edge of the belt such that there is overlap between the central chassis 38 by at least about 10 mm, or by at least about 15 mm, to secure integrity between the front and or back belt 84, 86 and central chassis 38.

Figure 2A:
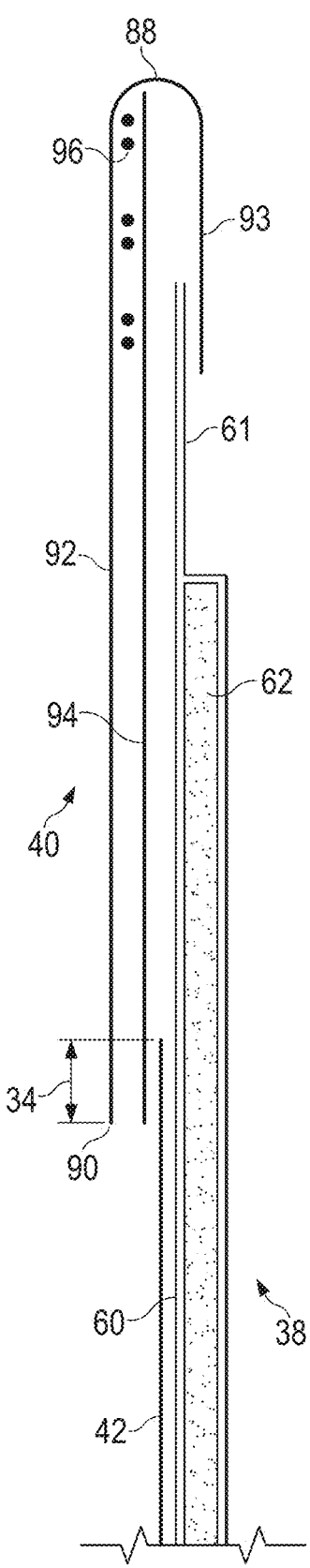
FIGS. 2A-2C are schematic cross section views of embodiments of wearable articles of the present invention
Figure 2B:
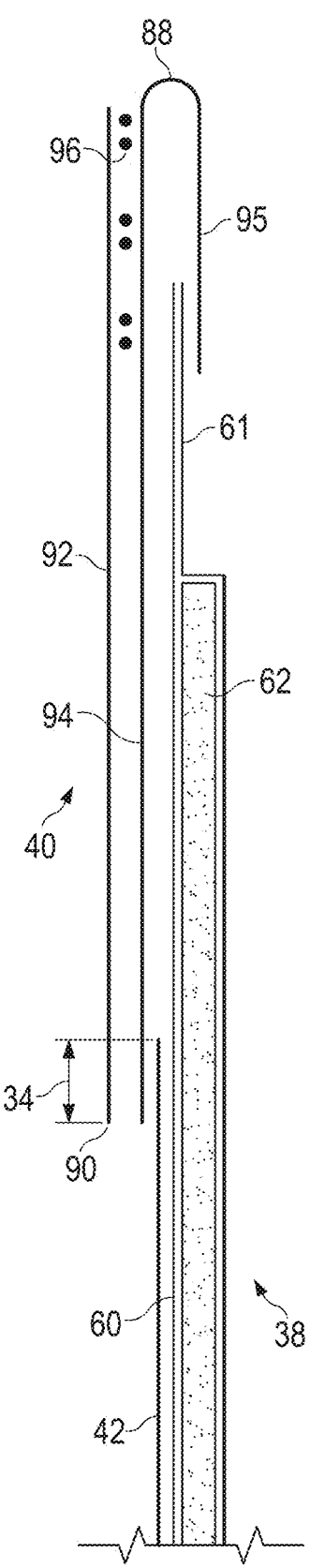
Figure 2C:
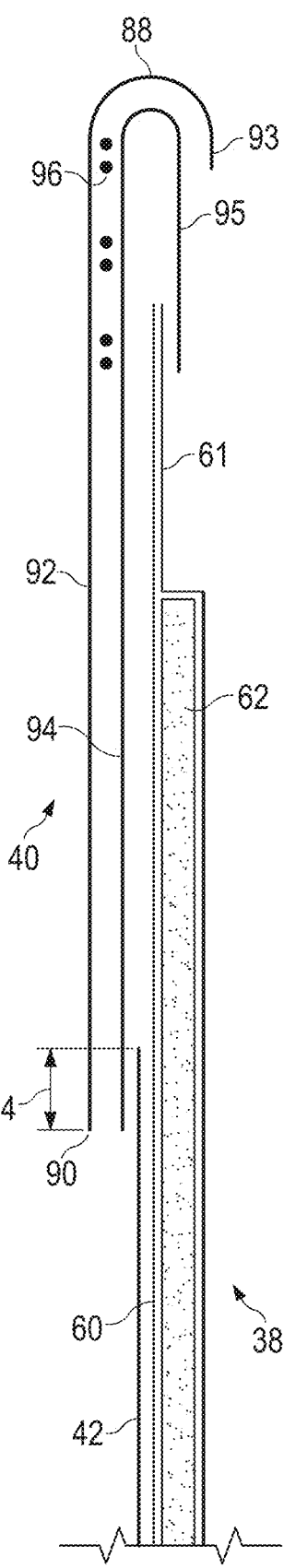

Referring to FIG. 2A, the front belt 84 and/or back belt 86 may comprise an outer web fold over 93 wherein the outer web fold over 93 is an extension of the outer web, the outer web fold over 93 formed by folding the extended portion of the outer web at the distal edge 88 of the belt. When the front belt 84 and/or back belt 86 is formed by the present elastic laminate, the outer web is extended beyond the elastic laminate, and folded over the inner web such that at least a portion of the elastic belt comprises one layer of the inner web sandwiched between two layers of the outer web.

Referring to FIG. 1A, the transverse width LW of the back belt 86 in the uncontracted condition may be the same as the transverse width of the front belt 84 of the same condition. Such an article may be economically made. The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams close the front and back belt 84, 86 side edges 89 of the same length for forming the article. Such an article may be economically made. The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90. In such configuration, when the wearable article is assembled to form the waist opening and the leg openings, the wearable article is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the central chassis 38 beyond the front proximal edge 90. The side edge of the proximal portion of the back side panel 82 may not be joined to anywhere and free from attachment. Thus, the proximal portion of the back side panel 82 provides a buttock cover.

Referring to FIGS. 1A and 2A-2C, the front and back belts 84, 86 may be discontinuous with one another in the crotch region 30, such that the outer cover layer 42 is the garment-facing surface in the crotch region 30. The outer cover layer 42 may extend only partly in the longitudinal direction of the front waist panel 52 and the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, providing better breathability and sweat management for the elastic belt 40. Further, this may provide cost saving of the outer cover layer 42 material. Accordingly, looking at the layers of elements between the garment facing surface and the backsheet 60 of the center chassis 38, there exists a transitional region 34 disposed on the front and back waist panel 52, 54 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for a wearable article in an economical manner, printing may be provided on the garment facing side of the backsheet 60. By providing the transitional region 34 as short as possible, applying adhesive to the transitional region 34 to enhance transparency, or simply avoiding displaying artwork in the transitional region 34, compromised appearance of the artwork over different layers of material between the artwork and the observer may be avoided. Referring to FIG. 1A, artwork on the backsheet 60 may be printed in regions 40F and/or 40B.

The articles of the present invention provide improved sweat management properties, are easy to apply and comfortable to wear, while being economic to make.

Bio-Based Materials

The elastic laminate may comprise a bio-based content value from about 10% to about 100% using ASTM D6866-10, method B, or from about 25% to about 75%, or from about 50% to about 60%.

The inner and outer web, and the first fibrous layer and/or the second fibrous layer of the inner or outer web of the elastic laminate may comprise a bio-based content value from about 10% to about 100% using ASTM D6866-10, method B, or from about 25% to about 75%, or from about 50% to about 60%.

In order to apply the methodology of ASTM D6866-10 to determine the bio-based content of a single component material (i.e., the elastic laminate), that material is isolated and cleaned such that the resulting specimen reflects the constituent starting material as closely as possible. For example, if a nonwoven component of an elastic nonwoven laminate is of interest, the laminate is deconstructed (with elastic strands removed) and the nonwoven layer is washed with an appropriate solvent so as to remove any residual adhesive present. In order to apply the methodology of ASTM D6866-10 to an sample assembly of two or more materials of differing or unknown compositions, the sample is homogenized by grinding the material into particulate form (with particle size of about 20 mesh or smaller) using known grinding methods (such as with a Wiley grinding mill). A representative specimen of suitable mass is then taken from the resulting sample of randomly mixed particles.

Validation of Polymers Derived from Renewable Resources

A suitable validation technique is through 14C analysis. A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized to carbon dioxide. This radioactive isotope represents a small but measurable fraction of atmospheric carbon. Atmospheric carbon dioxide is cycled by green plants to make organic molecules during photosynthesis. The cycle is completed when the green plants or other forms of life metabolize the organic molecules, thereby producing carbon dioxide which is released back to the atmosphere. Virtually all forms of life on Earth depend on this green plant production of organic molecules to grow and reproduce. Therefore, the 14C that exists in the atmosphere becomes part of all life forms, and their biological products. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the bio-based content of materials can be determined. ASTM International, formally known as the American Society for Testing and Materials, has established a standard method for assessing the bio-based content of materials. The ASTM method is designated ASTM D6866-10.

The application of ASTM D6866-10 to derive a "bio-based content" is built on the same concepts as radiocarbon dating, but without use of the age equations. The analysis is performed by deriving a ratio of the amount of organic radiocarbon (14C) in an unknown sample to that of a modern reference standard. The ratio is reported as a percentage with the units "pMC" (percent modern carbon).

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, for example, it would give a radiocarbon signature near 54 pMC (assuming the petroleum derivatives have the same percentage of carbon as the soybeans).

A biomass content result is derived by assigning 100% equal to 107.5 pMC and 0% equal to 0 pMC. In this regard, a sample measuring 99 pMC will give an equivalent bio-based content value of 92%.

Assessment of the materials described herein can be done in accordance with ASTM D6866. The mean values quoted in this report encompasses an absolute range of 6% (plus and minus 3% on either side of the bio-based content value) to account for variations in end-component radiocarbon signatures. It is presumed that all materials are present day or fossil in origin and that the desired result is the amount of biobased component "present" in the material, not the amount of biobased material "used" in the manufacturing process.

Test Methods

NMR Mouse Test Method

Figure 3:
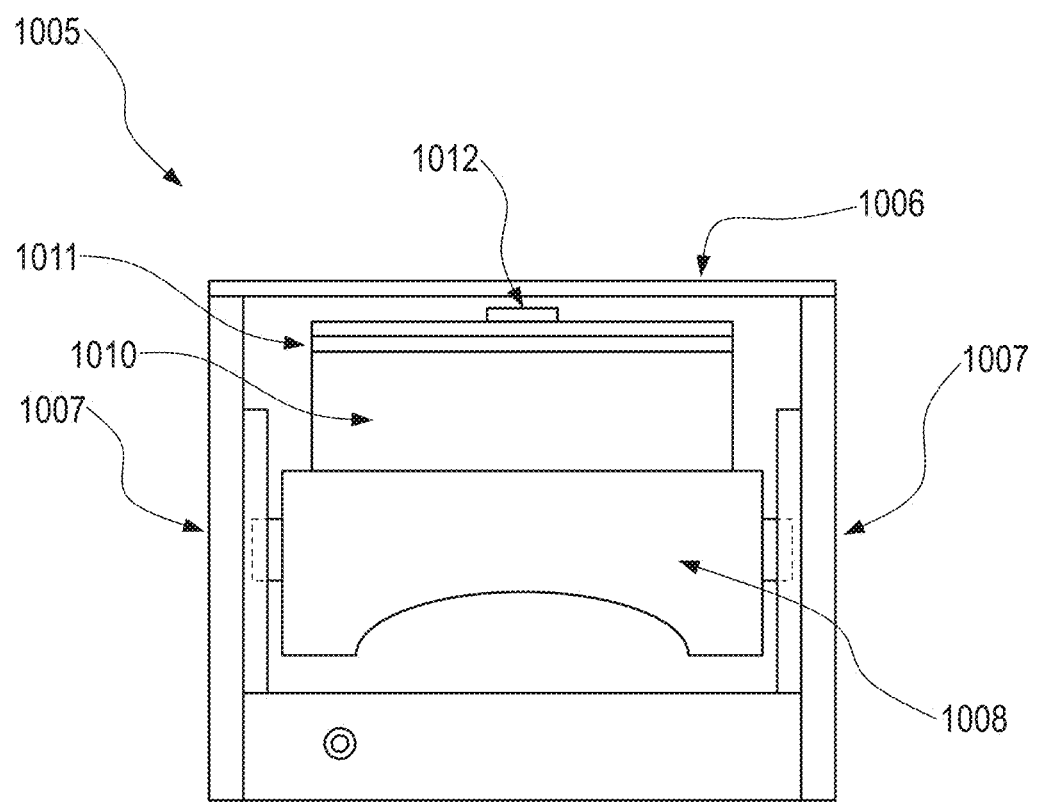
FIG. 3 shows a schematic representation of an NMR sensor

The NMR-MOUSE (Mobile Universal Surface Explorer) is a portable open NMR sensor equipped with a permanent magnet geometry that generates a highly uniform gradient perpendicular to the scanner surface (shown in FIG. 3). A frame 1007 with horizontal plane 1006, made of glass-fiber reinforced plastic, supports the specimen and remains stationary during the test. A flat sensitive volume of the specimen is excited and detected by a surface rf coil 1012 placed on top of the magnet 1010 at a position that defines the maximum penetration depth into the specimen. By repositioning the sensitive slice across the specimen by means of a high precision lift 1008, the scanner can produce one-dimensional profiles of the specimen's structure with high spatial resolution.

An exemplary instrument is the Profile NMR-MOUSE model PM25 with High-Precision Lift available from Magritek Inc., San Diego, CA. Requirements for the NMR-MOUSE are a 50 μm resolution in the z-direction, a measuring frequency of 13.5 MHz, a maximum measuring depth of 25 mm, a static gradient of 8 T/m, and a sensitive volume (x-y dimension) of 40 mm by 40 mm. Before the instrument can be used, perform phasing adjustment, check resonance frequency and check external noise level as per the manufacturer's instruction. All measurements are conducted in a room controlled at 23° C.±1° C. and 50%±2% relative humidity.

The test solution is prepared: 0.9% w/v saline solution prepared as 9.0 g of NaCl diluted to 1 L deionized water. 2 mM/L of Diethylenetriaminepentaacetic acid gadolinium (III) dihydrogen salt (available from SigmaAldrich) is added. After addition the solutions are stirred using a shaker at 160 rpm for one hour. Afterwards the solutions are checked to assure no visible undissolved crystals remain. The solution is prepared 10 hours prior to use. Products for testing are conditioned at 23° C.±1° C. and 50%±2% relative humidity for two hours prior to testing.

Identify the elastic laminate of the wearable article (e.g. at the back belt if the elastic laminate forms an elastic belt of the wearable article) and cut a 100.0 mm by 100.0 mm specimen from the clastic laminate. Ensure that only elastic laminate is cut out to enable a flat specimen 1022 on the frame. If the clastic laminate is attached to other components of the wearable article and a specimen cannot be cut without separating the clastic laminate, the elastic laminate should be carefully separated by appropriate techniques from those other components, e.g. by applying "Quik-Freeze®" type cold spray, or other suitable methods that do not permanently alter the properties of the elastic laminate.

Figure 4:
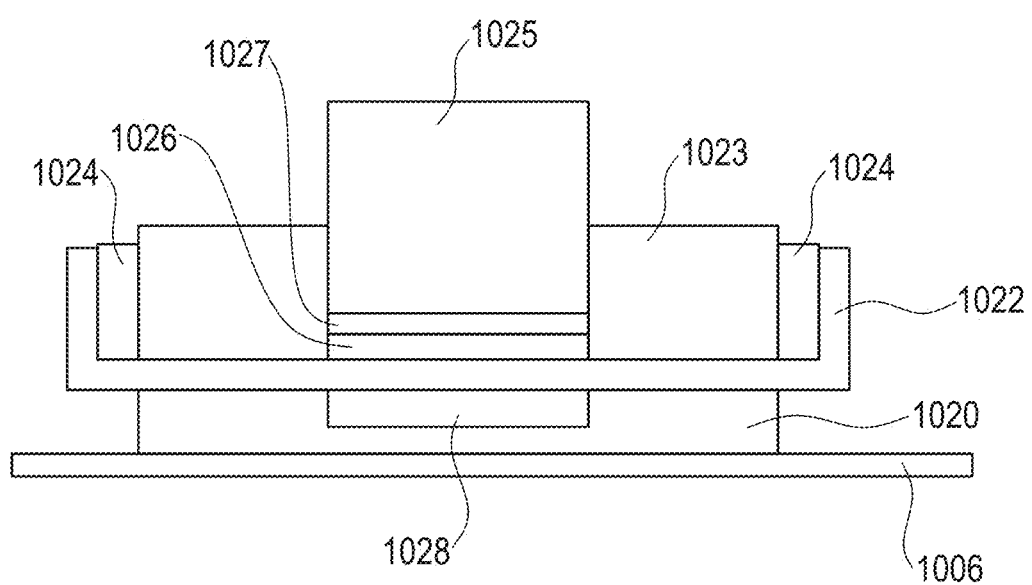
FIG. 4 shows a schematic representation of a specimen and equipment as prepared for and placed on the NMR MOUSE sensor

As illustrated in FIG. 4, the specimen 1022 is mounted on an 80 mm×80 mm×height of 20 mm frame 1023, made of polycarbonate with the surface of the outer web (as designated in the example section below) facing upwards using two pieces of double-sided tape 1024 on each edge to stretch the clastic laminate until the material is flat, i.e., the laminate shows no wrinkles. The frame has an opening area of 40 mm×40 mm into which a top marker is inserted. The top marker consists of a block 1025, made of polycarbonate and a glass plate 1026 which is mounted to the block 1025 with double-sided tape 1027 (glass slide 1026 and tape 1027 are shown in exaggerated dimension in FIG. 4). The block 1025 has a dimension of 40 mm×40 mm corresponding to the size of the opening area in the frame 1023. The high of the polymeric block is 30 mm. The glass plate 1026 has a thickness of 400 µm. The double-sided tape 1027 must be suitable to provide NMR Amplitude signal. When the specimen 1022 is mounted on the frame 1023, the first surface of the inner layer is facing towards the NMR MOUSE instrument. Ensure the 40 mm×40 mm opening area of the frame 1023, into which the top marker is inserted is covered by the specimen 1022.

Like the frame 1023, the sample holder 1020 has an opening 1028 of 40 mm×40 mm. The depth of the opening in the sample holder 1028 is 400 µm. The sample holder has a dimension of 80 mm×80 mm and a height of 1.4 mm (including the 400 µm depth). The sample holder 1020 is placed in the middle of the NMR MOUSE (above rf coil 1012) on plane 1006 to ensure that the sensitive NMR volume is within the 40 mm×40 mm opening 1028 where the liquid will be applied. Place the frame 1023 centered on top of the sample holder 1020, such that the top marker and opening 1028 are congruent and place the top marker onto the specimen 1022, such that glass plate 1026 is in contact with specimen 1022. The top marker is used to define the dimension of the specimen by determining the surface of the sample holder 1020 and the specimen 1022 in the 40 mm×40 mm opening area 1028.

First 1-D Dry Distribution Profiles with and without the specimen 1022 with the top marker onto the specimen are collected. A dry distribution profile is the NMR signal as a function of depth with a resolution of 50 µm. Ensure that the prepared specimen on the instrument is aligned over top the rf coil 1012. Program the NMR-MOUSE for a Carr-Purcell-Meiboom-Gill (CPMG) pulse sequence consisting of a 90° x-pulse follow by a refocusing pulse of 180° y-pulse using the following conditions:

Repetition Time=500 ms
Number of Scans=8
Number of Echoes=8
Resolution=50 µm
Step Size=−50 µm
Pulse Length=5 µs
Echo Time=90 µs
Echo Shift=1 µs Rx Phase of the NMR signal is optimized during the phase adjustment as described by the vendor to maximize the real part of the NMR signal which is used for data processing. A value of 230° was applied for our experiments. However, the optimal value may differ depending on the NMR instrument used, and hence the Rx phase should be optimized as described by the vendor. Pulse length for a 90° pulse depends on measurement depth which here is 5 mm and was determined to be 5 µs based on the optimization procedure described by the vendor. If necessary, the depth can be adjusted using a spacer 1011 (see FIG. 3).

Figure 5A:
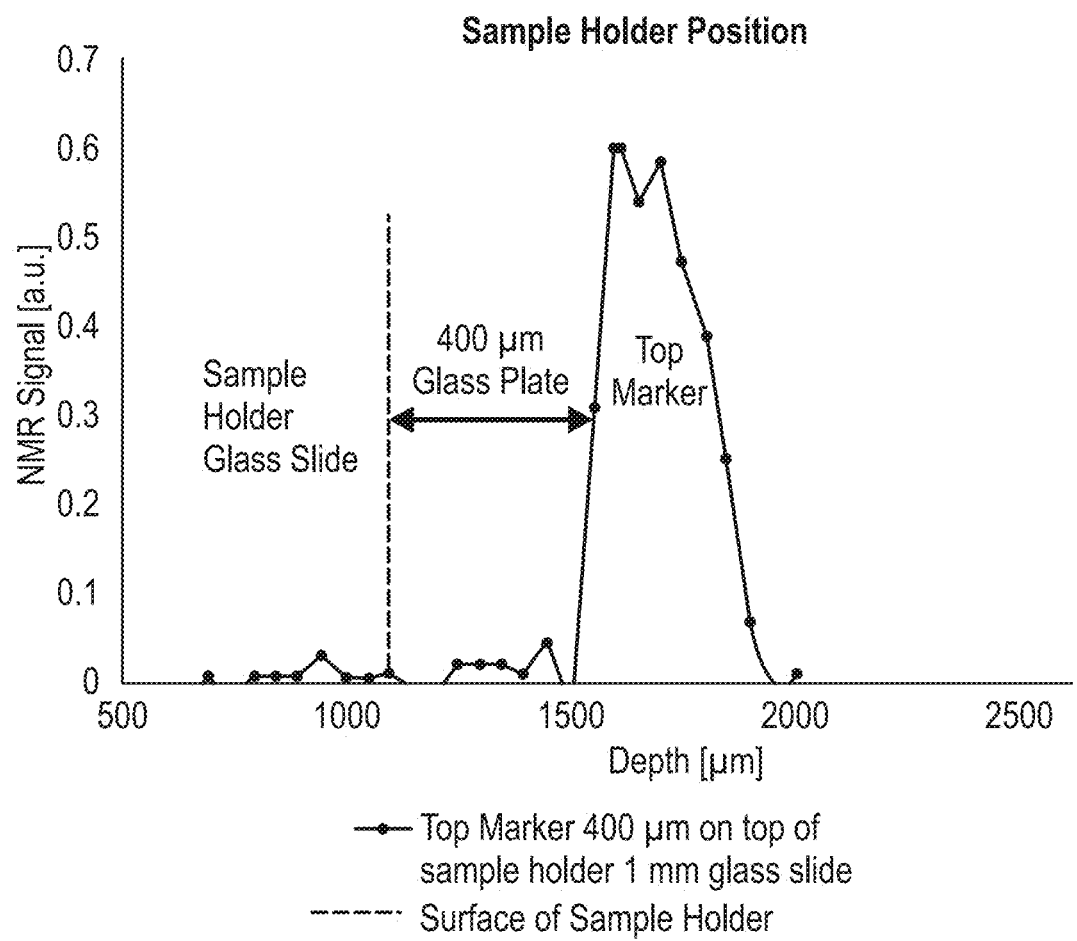
Figure 5B:
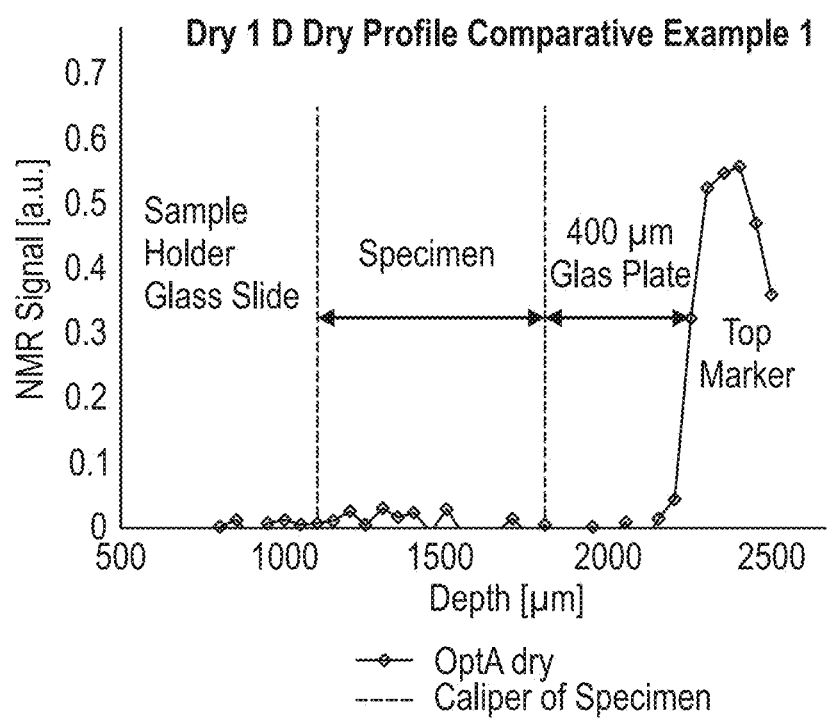

Collect NMR Amplitude data (in arbitrary units, a.u.) versus depth (µm) as the high precision lift steps through the specimen's depth. A representative graph with the dry specimen is shown in FIG. 5B and without the specimen is shown in FIG. 5A.

After the Dry Distribution Profile has been measured remove the top marker and the frame 1023 with the specimen 1022 attached thereto. Apply 400 µl of test solution (see above for preparation of test solution) in the opening 1028 of the sample holder 1020. Immediately afterwards place the frame 1023 with the specimen 1022 still attached thereto on top of the sample holder 1020. Measure the NMR 1-D Wet Distribution Profile in the wet state of the specimen 1 minute after the specimen 1022 has been brought into contact with the test solution. This profile is used to calculate the Liquid Ratio of the first 200 µm and last 200 µm sub-caliper to the total caliper value after one minute.

The NMR 1-D Wet Distribution Profile can also be used to calculate Liquid Ratio of the first 200 µm sub-caliper to the second total caliper after 10 minutes, and after 20 minutes, determined in the following way: Evaporation step is carried out with no additional air ventilation, i.e. evaporation is not accelerated by air ventilation. The frame with the specimen remains on top of the sample holder during the complete evaporation time. After 10 min evaporation time—without further waiting—the NMR 1-D Wet Distribution Profile is measured. This profile is used to calculate the Liquid Ratio of the first 200 µm and last 200 µm sub-caliper to the total caliper value after ten minutes. The "first 200 µm" is the sub-caliper which is facing towards the bottom of the sample holder, the "last 200 µm" is the sub-caliper which is facing away from the sample holder. The first 200 µm includes the first outwardly facing surface of the specimen. If the specimen is taken from an elastic laminate forming an elastic belt of the wearable article, the first outwardly facing surface is in contact with the skin of the wearer when the article is applied on a wearer. The last 200 µm includes the second outwardly facing surface of the specimen (which is opposite to the first outwardly facing surface). If the specimen is taken from an elastic laminate forming an elastic belt of the wearable article, the second outwardly facing surface is the garment-facing surface when the article is applied on a wearer and is not in direct contact with the wearer's skin.

The procedure is repeated to allow another 10 min evaporation of liquid through the specimen 1022 (like for the first 10 minutes, this evaporation step is carried out with no additional air ventilation, i.e. evaporation is not accelerated by air ventilation). Measure the NMR 1-D Wet Distribution Profile in the wet state of the specimen 20 minutes evaporation. This profile is used to calculate the Liquid Ratios of the first 200 µm and last 200 µm sub-caliper to the second total caliper value after twenty minutes.

When starting the evaporation time, no further test solution is filled in to the opening 1028, i.e. test solution is only filled in once, after the Dry Distribution Profile has been taken.

FIGS. 6A to 6D show the Dry Distribution Profiles, as well as the Wet Distribution Profiles after 1 minute, 10 and 20 minutes.

Figure 5C:
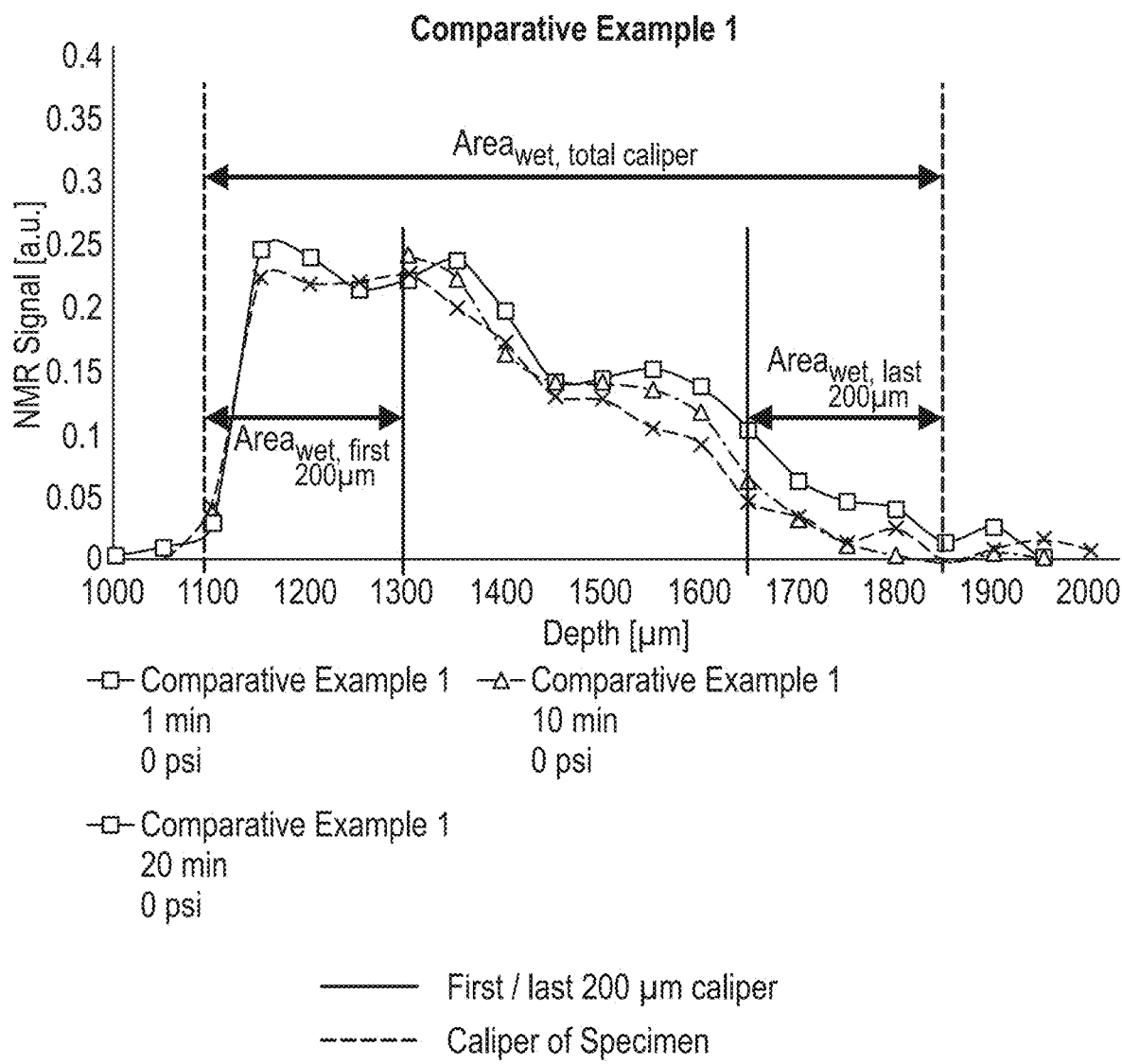
FIG. 5C shows the position of the sample holder determined without top marker, with wet specimen.
Figure 6A:
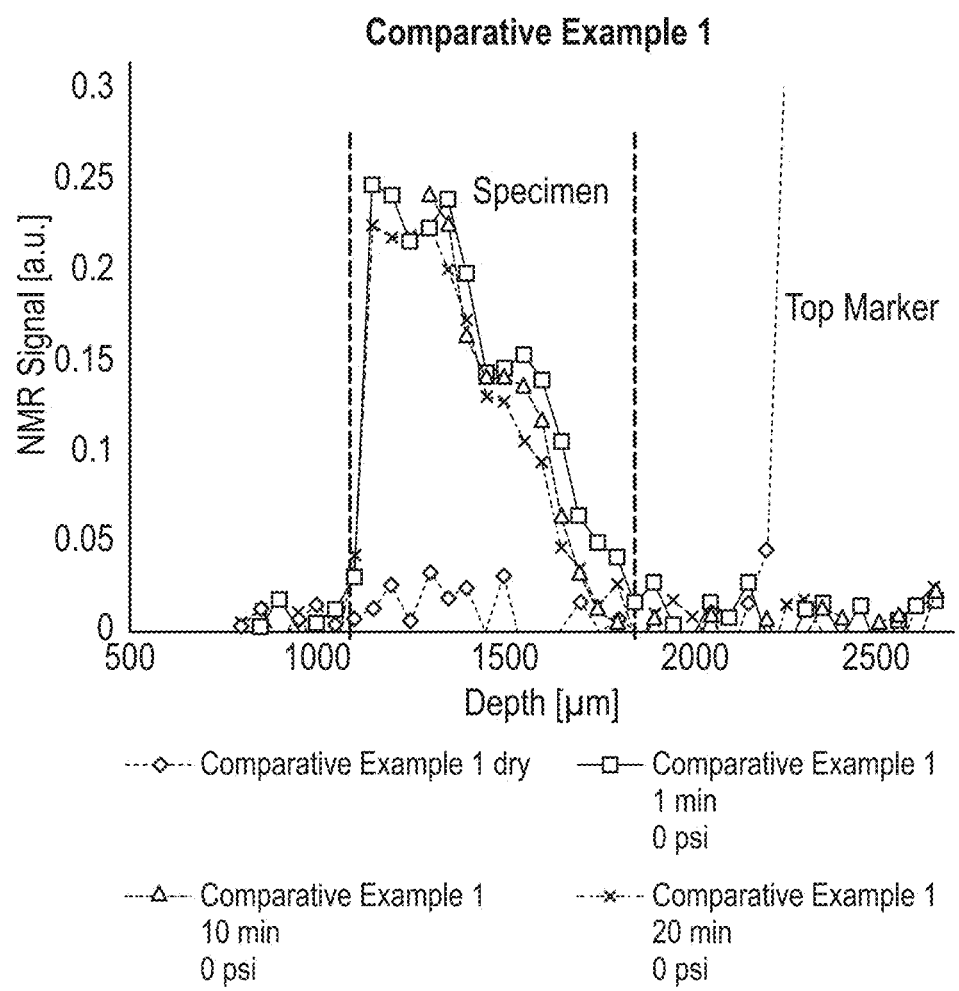
FIG. 6A shows the Dry Distribution Profile and Wet Distribution Profile (after 1 minute and 20 minutes) of Comparative Example 1
Figure 6B:
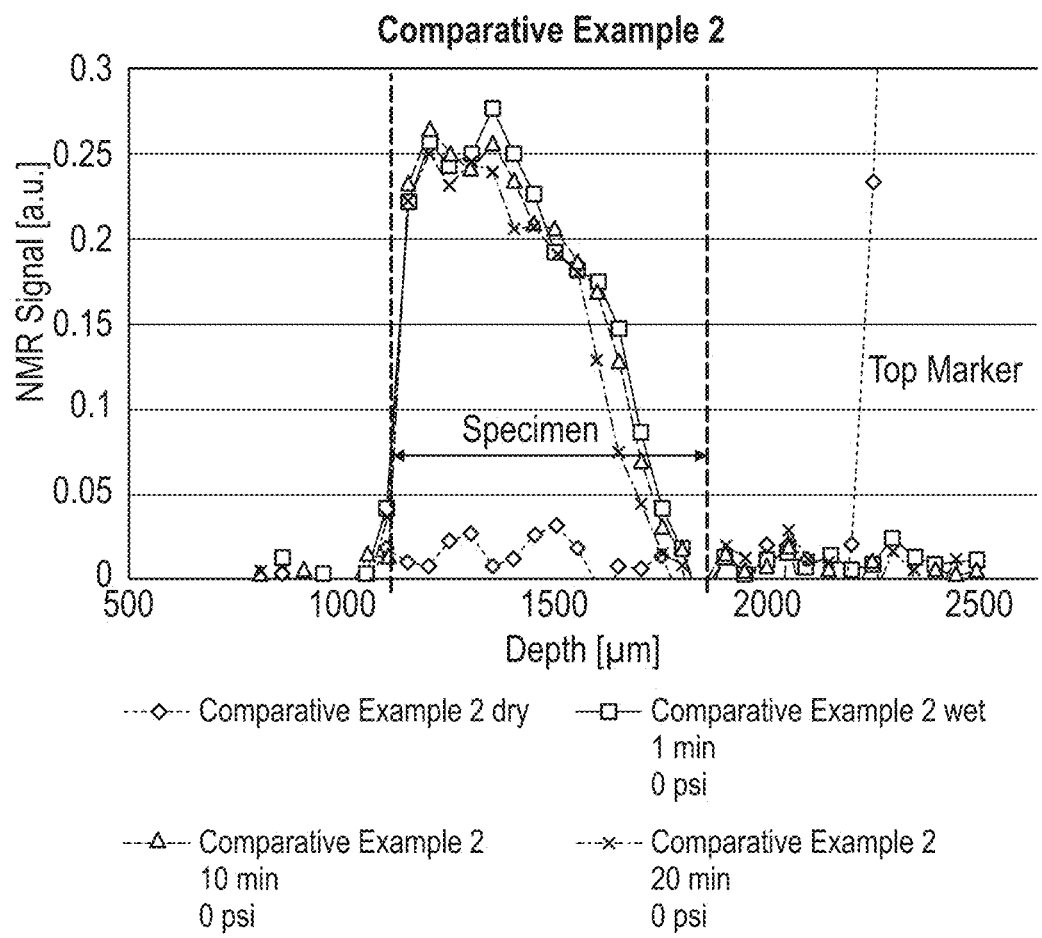
FIG. 6B shows the Dry Distribution Profile and Wet Distribution Profile (after 1 minute, 10 minutes and 20 minutes) of Comparative Example 2
Figure 6C:
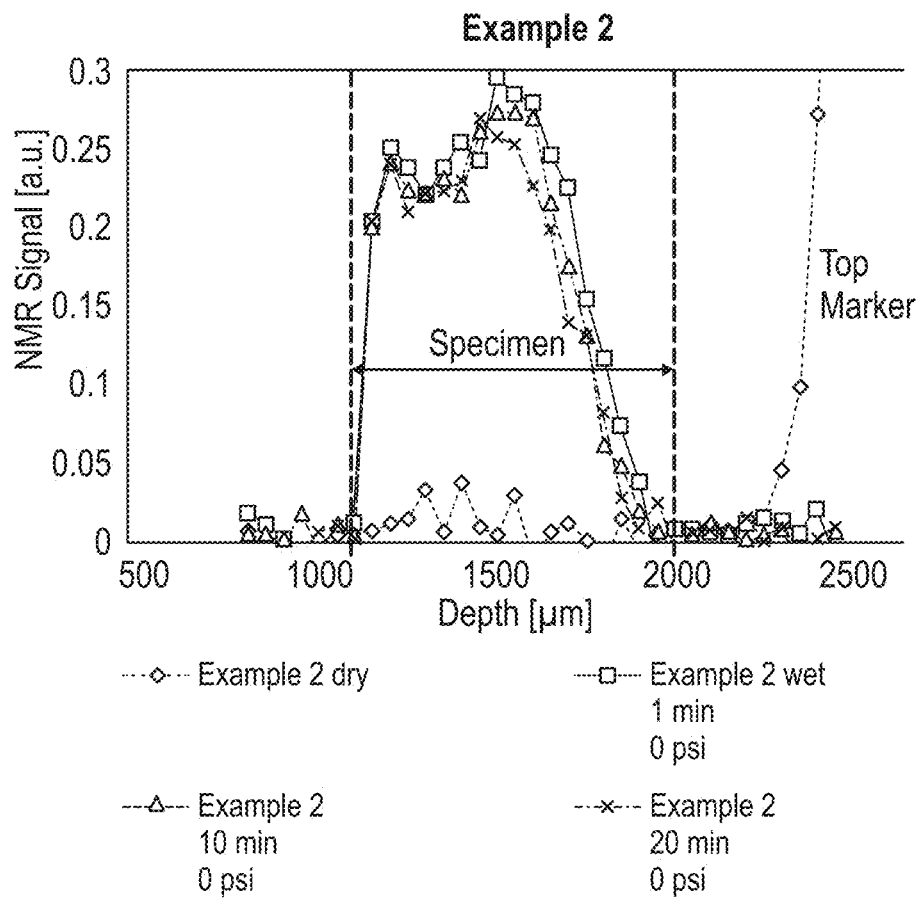
FIG. 6C shows the Dry Distribution Profile and Wet Distribution Profile (after 1 minute, 10 minutes and 20 minutes) of Example 2
Figure 6D:
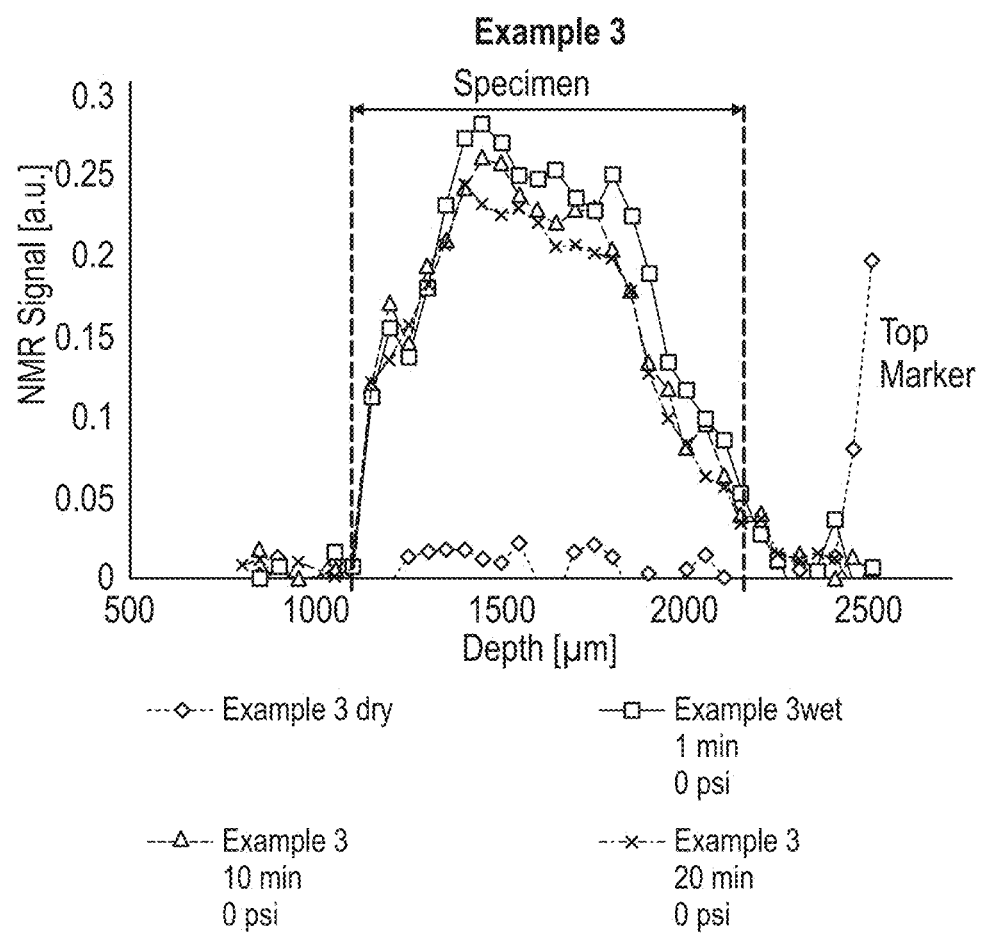
FIG. 6D shows the Dry Distribution Profile and Wet Distribution Profile (after 1 minute, 10 minutes and 20 minutes) of Example 3
Figure 7:
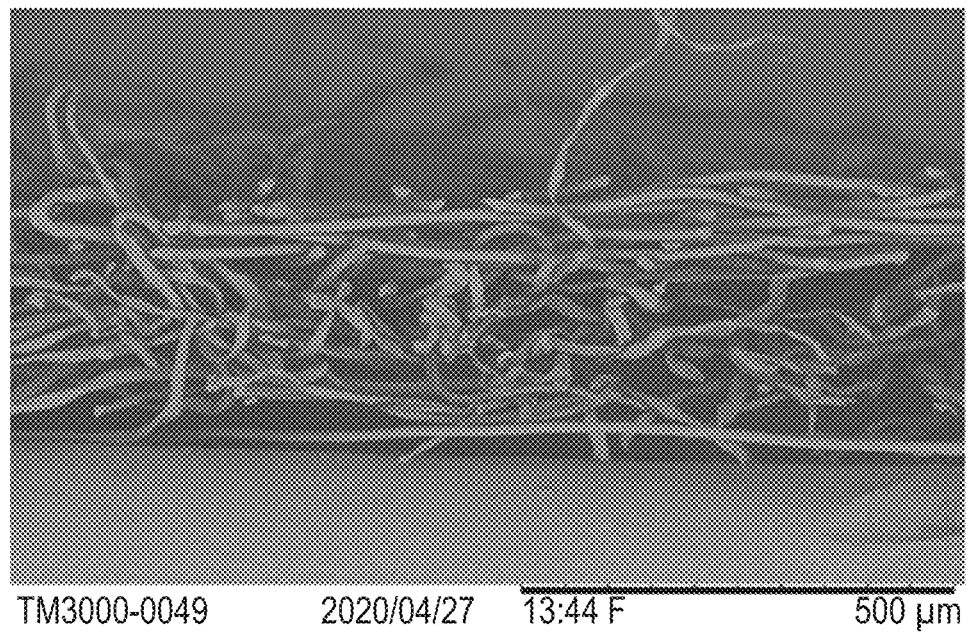
FIG. 7 shows a SEM photography of a outer web with first and second fibrous layer, wherein the upper side is the first fibrous layer (polypropylene fibers) and the bottom side is the second fibrous layer (cotton fibers). The SEM photography shows fibers of the second fibrous layer interpenetrating the fibers of the first fibrous layer. It can also be seen that the some fibers of the second fibrous layer penetrate through the first fibrous layer and outside of the first surface.

The liquid ratios of the first 200 µm and last 200 µm caliper to the total caliper is calculated as described below. FIG. 5C shows a typical example for the liquid distribution as a function of depth.

The area calculation is made for any range of caliper of interest such as the total caliper in the specimen (i.e., the total caliper of the elastic laminate), the first and the last 200 µm sub-caliper of the specimen (i.e., the first 200 µm sub-caliper of the elastic laminate), and the total caliper of the specimen (i.e. the total caliper of the elastic laminate):

$$\text{Area}_{Wet,Dry} = \sum_{i=1}^{n}(X_{i+1} - X_i) \times \frac{(S_{i+1} + S_i)}{2}$$

Where $X_i$ is the depth in μm corresponding to a data point, $S_i$ is amplitude of the corresponding NMR Signal, and n is the overall number of the data points.
Determine the liquid ratio of the first 200 μm vs. total caliper of the specimen. product.

% Liquid Ratio[%]$_{first\ 200\ \mu m}$ =

$$\frac{\text{Area}_{wet,first\ 200\ \mu m} - \text{Area}_{dry,first\ 200\ \mu m}}{\text{Area}_{wet,total\ caliper} - \text{Area}_{dry,total\ caliper}} * 100\%$$

Similarly, the liquid volume present in the last 200 μm of the specimen as a percentage of the liquid volume in the total caliper is calculated in the following way:

% Liquid Ratio[%]$_{last\ 200\ \mu m}$ =

$$\frac{\text{Area}_{wet,last\ 200\ \mu m} - \text{Area}_{dry,last\ 200\ \mu m}}{\text{Area}_{wet,total\ caliper} - \text{Area}_{dry,total\ caliper}} * 100\%$$

Where the liquid ratio [%] is the remaining liquid in the first 200 μm or the last 200 μm of the specimen to the total caliper of the specimen shown in FIG. 5C. The total caliper of the flattened out elastic laminate is determined by using the position of the top marker on top of the sample holder without any specimen shown in FIG. 5A and the position of the top marker out of the 1 D Dry Profile, see FIG. 5B where total caliper of the elastic laminate is "caliper of specimen".

Each measurement (Dry Distribution Profile, Wet Distribution Profile after 1 minute) is taken on one specimen only. Corresponding to each Wet Distribution Profile measured, a % Liquid Ratio [%] in first 200 micron/total Caliper and % Liquid Ratio [%] in last 200 micron/total Caliper are calculated and reported in percentage to the nearest tenth.

Contact Angle Test Method

A rectangular specimen of the web, measuring 1 cm×2 cm, is removed from the elastic laminate of a wearable article so as not to disturb the structure of the material. The specimen has a length of (2 cm) aligned parallel to the longitudinal centerline of the article. The specimen of interest may be separated from the other components of the wearable article such as the inner web or the outer web of the elastic laminate, elastic bodies between the inner and outer web, or backsheet or any other material by techniques such as applying freeze spray, or other suitable methods that do not permanently alter the properties of the web. The extracted web specimen is conditioned at a temperature of 23±2° C. and a relative humidity of 50±10% for at least 24 hours. The specimen is handled gently throughout by the edges using forceps and is mounted flat on an SEM specimen holder using double-sided tape. Multiple specimens are prepared in similar fashion as needed to accumulate the requisite number of individual measurements.

The specimen is sprayed with a fine mist of water droplets generated using a small hobby air-brush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Cryo-SEM prep chamber at −150° C. coated with Au/Pd for 2 minutes, and transferred into Cryo-SEM chamber at −150° C. A Gatan Alto 2500 Cryo-SEM prep chamber or equivalent instrument is used as preparation chamber. A Hitachi S-4700 Cryo-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. The contact angle between the droplet and the fiber is determined directly from the image.

The above procedure is used on the inner web to determine the Inner Web Contact Angle (if the inner web does not comprise a first and a second fibrous layer). Ten droplets, located on the inner web, are imaged from which 20 contact angle measurements are performed (one on each side of each imaged droplet), and the arithmetic mean of these 20 contact angle measurements is calculated and reported as the Inner Web Contact Angle to the nearest 0.1 degree.

The above procedure is used on the outer web to determine the Outer Web Contact Angle (if the outer web does not comprise a first and a second fibrous layer). Ten droplets, located on the outer web, are imaged from which 20 contact angle measurements are performed (one on each side of each imaged droplet), and the arithmetic mean of these 20 contact angle measurements is calculated and reported as the Outer Web Contact Angle to the nearest 0.1 degree.

The above procedure is used on the first fibrous layer of the inner or outer web (depending which of the inner and outer web is formed of a first and a second fibrous layer) to determine the Outer Web First Fibrous Layer Contact Angle or the Inner Web First Fibrous Layer Contact Angle. Ten droplets, located on the first fibrous layer of the inner or outer web, are imaged from which 20 contact angle measurements are performed (one on each side of each imaged droplet), and the arithmetic mean of these 20 contact angle measurements is calculated and reported as the Outer Web First Fibrous Layer Contact Angle to the nearest 0.1 degree or, if the inner web is formed of a first and second fibrous layer, is reported as the Inner Web First Fibrous Layer Contact Angle. The ten droplets are analyzed from portions of fibers located within a distance from the first surface of the outer web, wherein such distance is 20% of the outer web caliper.

The above procedure is used on the second fibrous layer of the inner or outer web (depending which of the inner and outer web is formed of a first and a second fibrous layer) to determine the Outer Web Second Fibrous Layer Contact Angle or the Inner Web Second Fibrous Layer Contact Angle. Ten droplets, located on the second fibrous layer of the inner or outer web, are imaged from which 20 contact angle measurements are performed (one on each side of each imaged droplet), and the arithmetic mean of these 20 contact angle measurements is calculated and reported as the Outer Web Second Fibrous Layer Contact Angle to the nearest 0.1 degree or, if the inner web is formed of a first and second fibrous layer, is reported as the Inner Web Second Fibrous Layer Contact Angle. The ten droplets are analyzed from portions of fibers located within a distance from the second surface of the inner or outer web, wherein such distance is 20% of the outer web caliper or, if the inner web is formed of a first and second fibrous layer, such distance is 20% of the inner web caliper.

Moisture Absorption Capacity Test Method

The Moisture Absorption Capacity C of a web can be measured as follows:

The web may be available as raw material or be removed from the wearable article. In order to remove from the wearable article, multiple specimens of the web, are removed from the elastic laminate of a wearable article, taking care not to touch the surface of the specimen or to disturb the structure of the material. Each specimen may be separated from the other components of the wearable article such as the inner web or the outer web of the elastic laminate, elastic bodies between the inner and outer web, or backsheet or any other material by techniques such as applying freeze spray, or other suitable methods that do not permanently alter the properties of the web. The sample of the webcan be removed from one specimen of the wearable article or combined from multiple specimen of the same wearable article in order to extract about 1 g of the web. The extracted web specimen is conditioned at a temperature of 23° C.±2° C. and a relative humidity of 50%±10% for at least 24 hours. The specimen is handled gently by the edges using forceps.

- Condition a dry amount of about 1 g of web (the sample) within a chamber at constant temperature and humidity (20° C., 60% RH) for 24 hours.
- Subsequently, subject the sample to moisture absorption for 2 hours within a chamber at constant temperature and humidity (40° C., 60% RH). Immediately after the 2 hours, determine the wet mass (MWET) of the sample.
- Then dry the sample within an oven for 24 hours at a temperature of 105° C.±/−3° C. and with 60% RH.
- Determine the dry mass (MDRY) of the sample.
- Calculate Moisture Absorption Capacity C as (MWET-MDRY)/MDRY in grams of moisture/grams of dry sample.

Average Surface Area/Volume Test Method

The Average Surface Area Per Volume Method uses analysis with a scanning electron microscope (SEM) to determine the average surface area per volume of each of one or more fibrous layers present in a web as well as to determine the average surface area per volume of a web (such as the inner web) as whole. SEM images containing front-face views and/or cross-sections of fibers are used to measure the perimeter per cross sectional area of individual fibers, which is deemed to correspond directly to the surface area per volume ratio of these same fibers, from which average surface area per volume present in each layer or web, respectively, is determined.

A rectangular specimen of the web, measuring 1 cm×2 cm, is removed from the elastic laminate of a wearable article taking care not to disturb the structure of the material. The specimen has a length of (2 cm) aligned with a longitudinal centerline of the wearable article. The specimen of interest may be separated from the other components of the wearable article such as the inner web and the outer web (which may represent the inner web or the outer web of the elastic laminate if used as an elastic belt), elastic bodies between the inner and outer web, or backsheet or any other material by techniques such as applying freeze spray, or other suitable methods that do not permanently alter the properties of the web. The extracted web specimen is conditioned at a temperature of 23±2° C. and a relative humidity of 50±10% for at least 24 hours. The specimen is handled gently throughout by the edges using forceps and is mounted flat on an SEM specimen holder using double-sided tape. Multiple specimens are prepared in similar fashion as needed to accumulate the number of measurements. In instances in which cross sectional analysis is performed, as described below, a new single-edged razor blade (such as 0.009" (0.22 mm) thick surgical carbon steel razor blade (part number 55411-050 from VWR, Radnor, PA, USA, or equivalent) is used to cross-section the specimen prior to mounting in the 2-cm dimension, and one of the fresh cross-sectional faces is subsequently analyzed in the SEM. Prior to introduction into the SEM, each specimen is sputtered with gold or a palladium compound to avoid electric charging and vibrations of the fibers in the electron beam A scanning electron microscope (SEM) is used to analyze the top view and cross section of the fibers.

A magnification of 500 to 10,000 times is chosen such that the ratio of target fiber perimeter to Horizontal Field Width (HFW) is bigger than 0.5. Secondary electron images are acquired with a standard Everhart-Thornley detector.

An initial cross-sectional SEM image of the web of interest is capture. If fibers present have a circular cross-section, then fiber-width measurements from top view images can be used as diameter, and corresponding perimeters (circumferences) are calculated for each diameter assuming circular cross sections. No fiber is measured more than once, and surface area to volume of each fiber measured is recorded as the circumference-to-area ratio at this point of measurement, i.e., $\pi D/((\pi D^2)/4)=4/D$, where D is the measured diameter of the fiber. If fibers present in the web do not have a circular cross-section, the area and perimeter for each fiber analyzed are directly measured from SEM cross-sectional web images. The use of image analysis software, such as Image J (NIH, Bethesda, MD, USA, or equivalent) may be used to aid in the accurate and facile measurement of cross-sectional perimeters. The perimeter and area of each cross section measured is recorded, as is the ratio of perimeter to area for each cross section.

If the web of interest exhibits a gradient in fiber size and/or shape, each distinct fibrous layer is separately characterized.

At least 100 measurements of individual fibers are performed for each fibrous layer in the web of interest, or in the web as a whole. The arithmetic mean of the ratios of cross-sectional perimeter to area recorded among fibers in each layer present is calculated, and this is reported as the average surface area per volume of that fibrous layer in the web of interest, or of the fibrous layer or web, respectively, of interest. The average surface area to volume ratio is reported in l/mm to the nearest 0.1 l/mm.

Fiber Diameter Test Method

The average equivalent fiber diameter of each of one or more distinct fiber(s) layer present in a web is done following the Average Surface Area Per Volume Method. Once the average surface area per volume (SApV) has been determined for a given fiber(s) layer, the average equivalent diameter for that fiber(s) layer is calculated as 4/SApV. The average equivalent fiber diameter is reported in micrometers (μm), to the nearest 0.1 μm.

Relative Opening Rate

Relative Opening Rate is the opening rate of the outer web and the inner web combined, compared to the opening rate of the outer web. Before preparation of specimen, the relationship of openings from the outer web and the inner web as the elastic laminate are observed. If the inner web has no openings, the Relative Opening Rate is determined as 0%. If the inner web has openings and the openings from the outer web and the inner web appear to completely or substantially match, the specimen is arranged as A). If the inner web has openings and the openings from the outer web and the inner web appear to partially match or not match, the specimen is arranged as B).
  A) The elastic laminate is treated according to the Preparation of specimen above to obtain the inner and outer webs. The inner and outer webs are overlayed such that the openings match each other as much as possible. The overlayed specimen is sent for measurement.
  B) The elastic laminate is treated according to the Preparation of specimen above to obtain the inner and outer webs. The inner and outer webs are overlayed in 2 different degrees of overlap of openings, one which has the openings matched as much as possible, and another which has the openings unmatched as much as possible. The 2 types of overlayed specimen are sent for measurement, respectively. The average Relative Opening Rate of the 2 types of overlayed specimen is obtained.

The overlayed specimen are measured in the same manner as specified under "2. Effective Opening Area and Opening Rate" to obtain the Opening Rate of the overlayed specimen.

The Relative Opening Rate is obtained as such. When there is a complete match between the inner web and the outer web, the Relative Opening Rate is 100%.

Relative Opening Rate (%)=Opening Rate of overlayed specimen/Opening Rate of outer web×100

Mean Flow Pore Size

Mean Flow Pore Size of nonwoven is characterized by the gas-liquid displacement method according to ASTM F316, using a capillary flow porometer such as Porolux™ 100 NW (Porometer N.V., Belgium). The porometry measurement follows the Young-Laplace equation, $P=4*\gamma*\cos(\theta)/D$, where D is the pore size diameter, P is the pressure measured, $\gamma$ is the surface tension of the wetting liquid, and $\theta$ is the contact angle of the wetting liquid with the sample. The procedures are the following:
  1) Wet the specimen with a liquid of low surface tension and low vapor pressure, for example, a commercial wetting liquid Porefil (Prorometer N.V., Belgium) with surface tension of 16 mN/m. Consequently, all pores are filled with the liquid.
  2) An inert gas is used to displace wetting liquid from pores and gas flow rate is normally measured using flow meters. The liquid is blown out of the specimen by gradually increasing the gas pressure. When further increasing the pressure, gas flows through small pores until all the pores are emptied. Record the gas pressure and gas flow rate when liquid is being expelled.
  3) After the wet run, the measurement of the same sample in dry state is carried out.
  4) The pore size parameters are calculated by comparing the pressure-flow rate curves from the wet run and dry run according to ASTM F316.

EXAMPLES

The following examples and comparative examples were tested (unless explicitly mentioned, the nonwoven webs were not apertured):

Comparative Example 1

Inner web: Spunbond nonwoven (SSS, i.e. three identical spunbond layers); 100% polypropylene; fiber diameter of about 15 μm; basis weight of 15 gsm. The nonwoven has been supplied by Fibertex under the tradename A10150AH.

Outer web: Carded air-through bonded nonwoven, bicomponent PE/PET 50% PET (core of bicomponent fibers), 50% polyethylene (shell of bicomponent fibers), fiber diameter of about 14.3 μm; basis weight of 20 gsm. The nonwoven has been supplied by Dayuan under the tradename FJ206.

Comparative Example 2

Inner web: same as inner web of Comparative Example 1
Outer web: Carded air-through bonded nonwoven, bicomponent PE/PET 50% PET, 50% polyethylene, fiber diameter of about 14.8 μm; basis weight of 22 gsm. The nonwoven has been supplied by Yanjan. Under the tradename Z05X-22.

Comparative Example 3

Inner web: 20 gsm air-through carded material made of PE/PET bicomponent fibers having fiber denier of 2 dpf, treated hydrophobically and apertured with tradename "J201-200", supplied by Xiamen Yanjan New Material Co. Ltd.
Outer web: 20 gsm air-through carded material made of PE/PET bicomponent fibers having fiber denier of 2 dpf, treated hydrophilically and apertured with tradename "DZ203-200", supplied by Xiamen Yanjan New Material Co. Ltd.

Comparative Example 4

Inner web: Same as outer web of Comparative Example 1
Outer web: 22 gsm PE/PET carded air-through nonwoven, hydrophilic Comparative Example 5

Inner web: 15 gsm spun calendar-bonded material made of hydrophobic PP monofilament, having fiber denier of 2 dpf, supplied by Fibertex
Outer web: 22 gsm PE/PET carded air-through nonwoven, hydrophilic.

Example 1

Inner web: Spunlace nonwoven, total basis weight 25 gsm; first fibrous layer is spunbond nonwoven (SSS), PP, fiber diameter of about 15.1 μm and basis weight of 11 gsm; second fibrous layer is cotton fibers with basis weight of 14 gsm (second fibrous layer is facing towards the outer web). First and second fibrous layers are combined via hydrojets in the spunlace process, such that at least some of the fibers of the second fibrous layer interpenetrate the fibers of the first fibrous layer. The nonwoven has been supplied by Yanjan under tradename FL08-25.
Outer web: Same as outer web of Comparative Example 2

Example 2

Inner web: Same as inner web of Example 1
Outer web: Spunbond nonwoven (SSS, i.e., three identical spunbond layers); 100% polypropylene; fiber diameter of about 16.2 μm; basis weight of 15 gsm. The nonwoven has been supplied by Fibertex under tradename A20150 KV.

Example 3

Inner web: same as outer web of Example 2
Outer web: same as inner web of Example 1, but second fibrous layer is facing towards the inner web.

Example 4

Inner web: Spunlace nonwoven, total basis weight 30 gsm; first fibrous layer is spunbond nonwoven (SSS), PP, fiber diameter of about 15.1 µm and basis weight of 11 gsm; second fibrous layer is cotton fibers with basis weight of 19 gsm (second fibrous layer is facing towards the outer web). First and second fibrous layers are combined via hydrojets in the spunlace process, such that at least some of the fibers of the second fibrous layer interpenetrate the fibers of the first fibrous layer. The nonwoven has been supplied by Yanjan under tradename FL08-30.
Outer web: Same as outer web of Comparative Example 2

Example 5

Inner web: same as outer web of Example 2
Outer web: same as inner web of Example 4, but second fibrous layer is facing towards the inner web.

For the NMR MOUSE test, the samples were formed to mimick the condition of folding over an extended portion the outer web over the inner web, such that the sample tested according to the NMR MOUSE test method had three layers, namely an inner web sandwiched between two outer webs (i.e. the outer web and the extended portion of the outer web). The samples were formed without elastic strand in between, and the inner and outer web were attached to each other with 5 gsm adhesive applied in spiral pattern. Test results refer to 1 minute after the specimen has been brought into contact with the test solution.

TABLE 1

Test results of NMR MOUSE test

| Example/<br>Comparative Example | % Liquid<br>Ratio [%] in<br>first 200 micron/<br>total Caliper<br>after 1 minute | % Liquid<br>Ratio [%] in<br>last 200 micron/<br>total Caliper<br>after 1 minute |
|---|---|---|
| Comparative Example 1 | 28.1 | 9.1 |
| Comparative Example 2 | 25.1 | 8.3 |
| Comparative Example 3 | 26.3 | 1.1 |
| Comparative Example 4 | 24.0 | 9.9 |
| Comparative Example 5 | 30.3 | 15.1 |
| Example 2 | 17.0 | 5.0 |
| Example 3 | 10.0 | 10.0 |

The first 200 micron is the sub-caliper starting from the surface facing downwards towards the bottom of the sample holder. The last 200 micron is the sub-caliper starting from the surface which is facing upwards. If the elastic laminate is used as an elastic belt, the first 200 micron start from the skin-facing surface of the elastic belt, extending through the thickness (=caliper) of the elastic laminate towards the garment-facing surface of the elastic laminate, and the last 200 micron would start from the garment-facing surface of the elastic laminate, extending through the thickness (=caliper) of the elastic laminate towards the skin-facing surface of the elastic laminate.

An in-use wear test with seven adults (hereinafter referred to as panelists) was performed with wearable articles in the form of adult incontinence pants. The panelists were asked not to shower or bath and not to exercise two hours before the start of the test, so skin was dry at the beginning of the test. Moreover, the panelists were advised not to use any creams, lotions and cosmetics on their skin for the 24 hours before the start of the test. Each of the seven panelists tested one sample of Comparative Examples 1 and 2 as well as Examples 4 and 6. Tests were carried out in random sample order by the panelists (Round robin scheduling).

The elastic laminates of the comparative examples and the examples formed an elastic belt of the pants. The outer web of the elastic belt comprised an extended portion which was extended beyond the front and back waist edge and which was folded over the inner web such that the fold forms the front and back waist edge and a portion of the elastic belt comprised the inner web sandwiched between the outer web and the extended portion of the outer web (=the 3-layered area). The extended portion extended respectively about 10 mm and about 40 mm from the front and back waist edge towards the crotch region.

After 15 minutes of acclimation period in a CTCH room (29° C.±/−1° C. and 50%±/−5% RH) (CTCH=Controlled Temperature Controlled Humidity), the panelists walked on an electric treadmill for 15 minutes at a speed between 3.5-4.5 Km/h in the CTCH room (29° C.±/−1° C. and 50%±/−5% RH). At the end of the treadmill walking phase, EWL (=Evaporative Water Loss) was measured via a Delfin Vapometer SWL-2 manufactured by Delfin Technologies, Finland, on the area of the skin of the panelist which was in contact with the 3-layered area, directly after removing the belt in the back. The vapometer is a stand alone device with pre-determined time (10 seconds) and algorithm calculation. We can refer to the user manual in the protocol.

Average EWL is reported in Table 3. Lower EWL indicates better performing elastic laminate with regard to transport of sweat away from the skin.

TABLE 2

| | Average EWL | | | |
|---|---|---|---|---|
| Option | Comparative<br>Example 1 | Comparative<br>Example 2 | Example 4 | Example 5 |
| Average EWL,<br>g/m²/h water<br>vapor | 230 | 214 | 196 | 182 |

According to NMR test, performed on a 3 layered sample (i.e. two outer webs with one inner web in between), Examples 2 and 3 show reduced % Liquid in the First 200 micron/total caliper on skin-facing side vs. the Comparative Examples while % Liquid in the Last 200 micron/total caliper on the outer side is comparable for Examples 2 and 3 relative to the Comparative Examples. This is consistent with the data for Average EWL, reflecting reduced skin hydration, for Examples 4 and 5.

TABLE 3

Characterization of inner and outer webs (average surface area/volume, contact angle)

| Sample | | average surface area/volume, 1/mm | Contact Angle, ° |
|---|---|---|---|
| Comparative Example 1 | Inner web | 266.8 | 93.0 |
| | Outer web | 280.6 | 86.8 |
| Comparative Example 2 | Inner web | 266.8 | 93.0 |
| | Outer web | 271.5 | 28.6 |
| Example 1 | Inner web | First fibrous layer: 279.1<br>Second fibrous layer 483.5 | First fibrous layer: 96.1<br>Second fibrous layer: 57.7 |
| | Outer web | 271.5 | 28.6 |
| Example 2 | Inner web | First fibrous layer: 279.1<br>Second fibrous layer: 483.5 | First fibrous layer: 96.1<br>Second fibrous layer: 57.7 |
| | Outer web | 247.9 | 37.5 |
| Example 3 | Inner web | 247.9 | 37.5 |
| | Outer web | First fibrous layer: 279.1<br>Second fibrous layer: 483.5 | First fibrous layer: 96.1<br>Second fibrous layer: 57.7 |

TABLE 4

Characterization of inner and outer webs; cosine of the contact angle θ multiplied with the average surface area per volume

| Sample | | Cos CA × average surface area/volume, 1/mm |
|---|---|---|
| Comparative Example 1 | Inner web | −14.0 |
| | Outer web | 15.7 |
| Comparative Example 2 | Inner web | −14.0 |
| | Outer web | 238.4 |
| Example 1 | Inner web | First fibrous layer: −29.7<br>Second fibrous layer: 258.4 |
| | Outer web | 238.4 |
| Example 2 | Inner web | First fibrous layer: −29.7<br>Second fibrous layer: 258.4 |
| | Outer web | 196.7 |
| Example 3 | Inner web | 196.7 |
| | Outer web | First fibrous layer: −29.7<br>Second fibrous layer: 258.4 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wearable article comprising an elastic laminate, the elastic laminate comprising
    an inner web and an outer web being in a face to face relationship, the inner and outer web each being a nonwoven web and each being comprised by the complete surface area of the elastic laminate,
    the elastic laminate having a skin-facing outer surface and a garment-facing outer surface,
    wherein at least a portion of the inner web is in direct contact with the skin of the wearer, and at least a portion of the outer web forms a garment-facing outer surface of the wearable article,
    the inner web having a first surface facing away from the outer web and a second surface facing towards the outer web,
    the outer web having a first surface facing towards the inner web and a second surface facing away from the inner web,
    the elastic laminate having a total caliper when subjected to the NMR MOUSE method as defined herein, the total caliper having a first 200 μm sub-caliper corresponding to 200 μm of the total caliper starting from the skin-facing outer surface of the elastic laminate and extending towards the garment-facing outer surface of the elastic laminate, and a last 200 μm sub-caliper corresponding to 200 μm of the total caliper starting from the garment-facing outer surface of the elastic laminate and extending towards the skin-facing outer surface of the elastic laminate, and
    wherein the elastic laminate has a % Liquid Ratio in the first 200 micron sub-caliper to total caliper of less than 20% after 1 minute according to the NMR MOUSE method set out herein.

2. The wearable article of claim 1, wherein the elastic laminate has a % Liquid Ratio in the last 200 micron sub-caliper to total caliper of not more than 20% after 1 minute according to the NMR MOUSE method set out herein.

3. The wearable article of claim 1, wherein the outer web is formed of a first fibrous layer and a second fibrous layer, the first and second fibrous layer being integrally combined with each other, and wherein at least some of the fibers of the second fibrous layer interpenetrate the fibers of the first fibrous layer, the first fibrous layer forming a first surface of the outer web and the second fibrous layer forming a second surface of the outer web, wherein the second surface faces towards the inner web and the first surface faces away from the inner web.

4. The wearable article of claim 3, wherein at least some of the fibers of the second fibrous layer interpenetrate the fibers of the first fibrous layer such that they protrude out of the first surface of the outer web.

5. The wearable article of claim 3, wherein
   a) the second fibrous layer is more hydrophilic than the first fibrous layer; and/or
   b) the second fibrous layer has higher surface area per volume than the first fibrous layer.

6. The wearable article of claim 3, wherein the first and second fibrous layer each have a contact angle θ and wherein the inner web has a contact angle θ, and
   wherein the cosine of the contact angle θ multiplied with the surface area per volume of the second fibrous layer is higher than the cosine of the contact angle θ multiplied with the surface area per volume of the inner web, and
   wherein the cosine of the contact angle θ multiplied with the surface area per volume of the second fibrous layer is higher than the cosine of the contact angle θ multiplied with the surface area per volume of the first fibrous layer.

7. The wearable article of claim 1, wherein the second fibrous layer is a carded layer and the fibers of the second fibrous layer are staple fibers.

8. The wearable article of claim 1, wherein the first fibrous layer is a spunbond layer formed of continuous fibers, or the first fibrous layer is a carded layer formed of staple fibers.

9. The wearable article of claim 1, wherein the first fibrous layer is a carded, air-through bonded layer formed of staple fibers, wherein the staple fibers are bicomponent fibers.

10. The wearable article of claim 1, wherein the first and second fibrous layer are integrally combined by spunlacing.

11. The wearable article of claim 1, wherein the fibers of the second fibrous layer have not been consolidated prior to being integrally combined with the fibers of the first fibrous layer.

12. The wearable article of claim 1, wherein no adhesive and/or no binder is used to combine the first and the second fibrous layer.

13. The wearable article of claim 1, wherein the second fibrous layer comprises natural hydrophilic fibers and/or modified hydrophilic fibers.

14. The wearable article of claim 13, wherein the amount of natural hydrophile fibers and/or man-modified hydrophilic fibers gradually increases through the thickness of the inner web from the first surface towards the second surface of the inner web.

15. The wearable article of claim 13, wherein the natural hydrophilic fibers or modified natural hydrophilic fibers are selected from the group consisting of cotton, bamboo, viscose, cellulose, silk, or mixtures or combinations thereof.

16. The wearable article of claim 1, wherein the elastic laminate does not comprise any further layer except the inner and outer web.

17. The wearable article of claim 1, wherein the total caliper of the elastic laminate is at least 450 μm.

18. The wearable article of claim 1, wherein the inner web comprises at least 70 weight-% of synthetic fibers based on the total basis weight of the inner web, and wherein the synthetic fibers of the inner web are selected from the group consisting of polyethylene, polypropylene, polyester, polylactic acid (PLA), and combinations thereof, and wherein the inner web does not comprise fibrous layers that are integrally combined with each other such that at least some of the fibers of the second fibrous layer interpenetrate the fibers of the first fibrous layer.

19. The wearable article of claim 1, wherein a plurality of elastic strands is provided between the inner and outer web.

20. The wearable article of claim 1, wherein the wearable article comprises a central chassis and a ring-like elastic belt, the ring-like elastic belt being formed of the elastic laminate and consisting of a front belt and a back belt; the center of the front belt being joined to a front waist panel of the central chassis, the center of the back belt being joined to a back waist panel of the central chassis, and the remainder of the central chassis forming a crotch region, the front and back belt each having a left side panel and a right side panel where the central chassis does not overlap, and the transverse edges of the front belt and the back belt being joined by a seam to form a waist opening made of a front and back waist edge, and also forming two leg openings; wherein the front belt and the back belt are discontinuous of each other in the crotch region in the longitudinal direction; and
   wherein the outer web comprises an extended portion which is extended beyond the front and back waist edge and which is folded over the inner web such that the fold forms the front and back waist edge and at least a portion of the elastic belt comprises the inner web sandwiched between the outer web and the folded over, extended portion of the outer web, and wherein the % Liquid Ratio in the first 200 micron sub-caliper to total caliper is less than 20% after 1 minute according to the NMR MOUSE method set out herein, the % Liquid Ratio being determined in the area of the elastic belt which comprises the inner web sandwiched between the outer web and the folded over, extended portion of the outer web.

21. The wearable article of claim 20, wherein the % Liquid Ratio in the last 200 micron sub-caliper to total caliper is not more than 20% after 1 minute according to the NMR MOUSE method set out herein, the % Liquid Ratio being determined in the area of the elastic belt which comprises the inner web sandwiched between the outer web and the folded over, extended portion of the outer web.

* * * * *